United States Patent [19]

Matthews et al.

[11] Patent Number: 5,525,633
[45] Date of Patent: Jun. 11, 1996

[54] TRIARYL-ETHYLENE DERIVATIVES

[75] Inventors: Donald P. Matthews, Indianapolis, Ind.; Alan J. Bitonti, Maineville; William A. Van Sickle, Loveland, both of Ohio; Donald A. Kaplan, Marina Del Rey, Calif.

[73] Assignee: Merrell Dow Pharmaceuticals Inc., Cincinnati, Ohio

[21] Appl. No.: 259,797

[22] Filed: Jun. 15, 1994

Related U.S. Application Data

[63] Continuation-in-part of Ser. No. 126,614, Sep. 24, 1993, abandoned.

[51] Int. Cl.$^6$ .................... A61K 31/135; C07C 211/28
[52] U.S. Cl. ............... 514/648; 514/237.8; 514/238.8; 514/255; 514/315; 514/317; 514/331; 514/357; 514/408; 514/428; 514/649; 514/651; 514/824; 544/165; 544/174; 544/396; 546/229; 546/336; 548/569; 548/575; 564/323; 564/324; 564/325; 564/326
[58] Field of Search .................... 564/323, 324, 564/325, 326; 514/648, 649, 651, 824, 237.8, 238.8, 255, 315, 317, 331, 357, 408, 428; 544/165, 174, 396; 546/229, 336; 548/569, 575

[56] References Cited

U.S. PATENT DOCUMENTS

| | | | |
|---|---|---|---|
| 2,914,563 | 11/1959 | Allen et al. | 260/570 |
| 3,247,252 | 4/1966 | Palopoli et al. | 260/570 |
| 3,634,517 | 1/1972 | Palopoli et al. | 260/590 |
| 4,623,660 | 11/1986 | Richardson . | |

FOREIGN PATENT DOCUMENTS

| | | |
|---|---|---|
| 0002097 | 5/1979 | European Pat. Off. . |
| 1013907 | 9/1962 | United Kingdom . |
| 1013907 | 12/1965 | United Kingdom . |
| 1099093 | 1/1968 | United Kingdom . |
| 1128379 | 9/1968 | United Kingdom . |

OTHER PUBLICATIONS

Murphy et al., "Structural Requirements for Binding of Anti estrogens" etc., *Rational Basis for Chemotherapy* pp. 195–210, (1983), Alan R. Lisa, Inc. ed., NY.

Watts et al., "Microsonal Binding Sites, etc," J of Biological Chemistry (1984), vol. 259, #7 pp. 4223–4229.

Palopoli III, "Substituted Aminoalkoxy trianylhaloethylenes," *J. Med. Chem*, vol. 10, pp. 84–86 (1967).

Palopoli, et al., *J. Med. Chem.*, 10:84–86 (Jan./1967).

Murphy, et al., *Biochemical and Biophysical Research Communications*, vol. 100(3):1353–1360 (Jun. 16, 1981).

Hecker, et al., *Europ. J. Cancer*, 10:747–749 (1974).

Herbst, et al., *Cancer Chemotherapy Reports*, 43:39–41 (Dec./1964).

Murphy, et al., *J. of Clinical Endocrinology and Metabolism* 57(2):373–379 (1983).

Murphy, et al., *Ludwig Institute for Cancer Research* (Sydney Branch), AU, *Rational Basis for Chemotherapy*, pp. 195–210, 1983, Alan R. Lisa, Inc., ed., N.Y.

Clark, et al., *Pharm. Ther*, vol. 15:467–519 (1982).

Legha, et al., *Cancer Treatment Reviews*, 3:205–216 (1976).

Watts, et al., *Jour. of Biological Chemistry*, vol. 259(7), 4223–4229 (1984).

*Primary Examiner*—Peter O'Sullivan
*Attorney, Agent, or Firm*—David M. Stemerick; Louis J. Wille

[57] ABSTRACT

The present invention relates to novel triaryl-ethylene derivatives that are useful as anti-neoplastic agents, antiatherosclerotic agents, and hypocholesterolemic agents.

15 Claims, No Drawings

TRIARYL-ETHYLENE DERIVATIVES

This application is a continuation-in-part of application Ser. No. 08/126,614, filed Sep. 24, 1993, now abandoned.

The present invention relates to novel triaryl-ethylene derivatives that are useful as antineoplastic agents, antiatherosclerotic agents, and hypocholesterolemic agents.

The present invention provides novel triaryl-ethylene derivatives of formula:

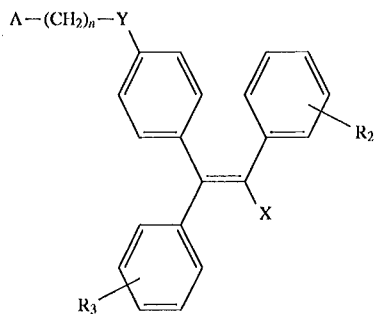

Formula I wherein

A is a radical of the formula

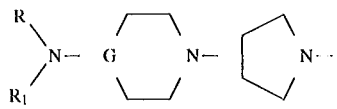

wherein

R and $R_1$ are each independently hydrogen or $C_1$-$C_4$ alkyl; and

G is HN, $H_3$CN, $CH_2$; or O;

n is an integer from 4 to 12;

$R_2$ is hydrogen, $C_1$-$C_4$ alkyl, $C_1$-$C_4$ alkoxy, halogen, or hydroxy;

$R_3$ is hydrogen, $C_1$-$C_4$ alkyl, $C_1$-$C_4$ alkoxy, halogen, hydroxy, or —$Y(CH_2)_p A_1$ in which $A_1$ is a radical of the formula

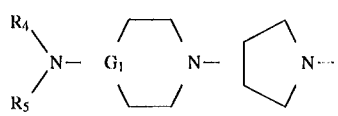

wherein $R_4$ and $R_5$ are each independently hydrogen or $C_1$-$C_4$ alkyl;

$G_1$ is HN, $H_3$CN, $CH_2$, or O; and p is an integer from 4 to 12;

X is chloro or bromo;

Y is O or NH;

or a pharmaceutically acceptable salt thereof.

In addition, the present invention provides triaryl-ethylene derivatives of the formula:

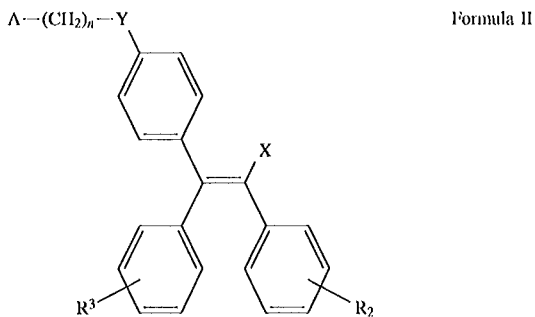

Formula II wherein

A is a radical of the formula

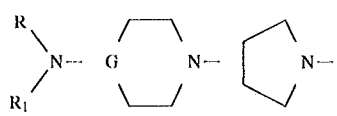

wherein

R and $R_1$ are each independently hydrogen or $C_1$-$C_4$ alkyl; and

G is HN, $H_3$CN, $CH_2$, or O;

n is an integer from 4 to 12;

$R_2$ is hydrogen, $C_1$-$C_4$ alkyl, $C_1$-$C_4$ alkoxy, halogen, or hydroxy;

$R_3$ is hydrogen, $C_1$-$C_4$ alkyl, $C_1$-$C_4$ alkoxy, halogen, hydroxy, or —$Y(CH_2)_p A_1$ in which $A_1$ is a radical of the formula

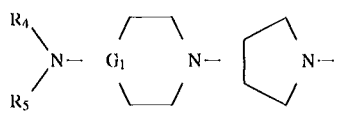

wherein $R_4$ and $R_5$ are each independently hydrogen or $C_1$-$C_4$ alkyl;

$G_1$ is HN, $H_3$CN, $CH_2$, or O; and p is an integer from 4 to 12;

X is chloro or bromo;

Y is O or NH;

or a pharmaceutically acceptable salt thereof.

Another embodiment of the present invention is a method of treating a patient afflicted with a neoplastic disease state or of controlling the growth of a neoplasm in a patient afflicted with a neoplastic disease state comprising administration of a therapeutically effective antineoplastic dose of a compound of Formulas I or II.

Another embodiment of the present invention is a method of prophylactically treating a patient at risk of developing a neoplastic disease state comprising administration of a prophylactically effective antineoplastic dose of a compound of Formulas I or II.

Another embodiment of the present invention is a method of treating hypercholesterolemia in patients suffering therefrom comprising the administration of a therapeutically effective hypocholesterolemic dose of a compound of Formulas I or II.

Another embodiment of the present invention is a method of treating atherosclerosis in patients suffering therefrom comprising the administration of a therapeutically effective antiatherosclerotic dose of a compound of Formulas I or II.

Another embodiment of the present invention is a method of treating hypercholesterolemia and atherosclerosis in patients suffering therefrom comprising the administration of a therapeutically effective antiatherosclerotic or a therapeutically effective hypocholesterolemic dose of a compound of Formulas I or II.

DETAILED DESCRIPTION OF THE INVENTION

As used herein, the term "$C_1$–$C_4$ alkyl" refers to a saturated, straight or branched chain, hydrocarbon radical of one to four carbon atoms and includes methyl, ethyl, propyl, isopropyl, n-butyl, isobutyl, t-butyl and the like.

As used herein, the designation " " refers to a bond for which the stereochemistry is not designated.

As used herein, the term "halogen" refers to a fluorine, chlorine, bromine, or iodine atom.

As used herein, the term "$C_1$–$C_4$ alkoxy" refers to a $C_1$–$C_4$ alkyl bearing an oxy group and includes methoxy, ethoxy, n-propoxy, n-butoxy, iso-propoxy, iso-butoxy, t-butoxy, and the like.

As used herein, the term "hydroxy" or "hydroxy group" refers to a —OH radical.

As used herein, the term "$(CH_2)_n$" refers to a straight chain alkylene radical of from 4 carbon atoms to 12 carbon atoms for example; butyl, pentyl, hexyl, heptyl, octyl, nonyl, decyl, undecyl, and dodecyl.

As used herein, the term "$(CH_2)_p$" refers to a straight chain alkylene radical of from 4 carbon atoms to 12 carbon atoms for example; butyl, pentyl, hexyl, heptyl, octyl, nonyl, decyl, undecyl, and dodecyl.

As used herein, the term "pharmaceutically acceptable addition salt refers to either an acid addition salt or a basic addition salt.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, and sulfonic acids such as p-toluenesulfonic acid, methanesulfonic acid and 2-hydroxyethane sulfonic acid. Either the mono- or di-acid salts may be formed, and such salts may exist in either a hydrated or substantially anhydrous form.

Compounds of Formula I and Formula II exist as geometric isomers. Any reference in this application to one of the compounds represented by Formula I and Formula II is meant to encompass a specific geometric isomer. The specific geometric isomers can be separated and recovered by techniques known in the art such as chromatography on silica gel, chromatography on a reverse-phase adsorbent, or fractional recrystallization. As is well known by one of ordinary skill in the art the Cahn-Ingold-Prelog designation of (E)- and (Z)- for isomers of compounds of Formula I and Formula II depends on the nature of Y, X, n, p, A, $R_2$, and $R_3$. As is apparent to one of ordinary skill in the art compounds of Formula I or II in which the substituent $R_3$ is —Y$(CH_2)_p A_1$ and p=n and A=$A_1$ do not exist as geometrical isomers.

Illustrative Examples of compounds encompassed by the present invention include:

(E)-1-[4-(4-Diethylaminobutoxy)phenyl]-1,2-diphenyl-2-chloro-ethylene;

(Z)-1-[4-(4-Diethylaminobutoxy)phenyl]-1,2-diphenyl-2-chloro-ethylene;

(E)-1-[4-(5-Diethylaminopentoxy)phenyl]-1,2-diphenyl-2-chloro-ethylene;

(Z)-1-[4-(5-Diethylaminopentoxy)phenyl]-1,2-diphenyl-2-chloro-ethylene;

(E)-1-[4-(6-Diethylaminohexoxy)phenyl]-1,2-diphenyl-2-chloro-ethylene;

(Z)-1-[4-(6-Diethylaminohexoxy)phenyl]-1,2-diphenyl-2-chloro-ethylene;

(E)-1-[4-(7-Diethylaminoheptoxy)phenyl]-1,2-diphenyl-2-chloro-ethylene;

(Z)-1-[4-(7-Diethylaminoheptoxy)phenyl]-1,2-diphenyl-2-chloro-ethylene;

(E)-1-[4-(8-Diethylaminooctoxy)phenyl]-1,2-diphenyl-2-chloro-ethylene;

(Z)-1-[4-(8-Diethylaminooctoxy)phenyl]-1,2-diphenyl-2-chloro-ethylene;

(E)-1-[4-(9-Diethylaminononoxy)phenyl]-1,2-diphenyl-2-chloro-ethylene;

(Z)-1-[4-(9-Diethylaminononoxy)phenyl]-1,2-diphenyl-2-chloro-ethylene;

(E)-1-[4-(10-Diethylaminodecoxy)phenyl]-1,2-diphenyl-2-chloro-ethylene;

(Z)-1-[4-(10-Diethylaminodecoxy)phenyl]-1,2-diphenyl-2-chloro-ethylene;

(E)-1-[4-(11-Diethylaminoundecoxy)phenyl]-1,2-diphenyl-2-chloro-ethylene;

(Z)-1-[4-(11-Diethylaminoundecoxy)phenyl]-1,2-diphenyl-2-chloro-ethylene;

(E)-1-[4-(12-Diethylaminododecoxy)phenyl]-1,2-diphenyl-2-chloro-ethylene;

(Z)-1-[4-(12-Diethylaminododecoxy)phenyl]-1,2-diphenyl-2-chloro-ethylene;

(E)-1-[4-(4-Diethylaminobutylamino)phenyl]-1,2-diphenyl-2-chloro-ethylene;

(Z)-1-[4-(4-Diethylaminobutylamino)phenyl]-1,2-diphenyl-2-chloro-ethylene;

(E)-1-[4-(4-Diethylaminobutoxy)phenyl]-1,2-diphenyl-2-bromo-ethylene;

(Z)-1-[4-(4-Diethylaminobutoxy)phenyl]-1,2-diphenyl-2-bromo-ethylene;

(E)-1-[4-(4-Diethylaminobutylamino)phenyl]-1,2-diphenyl-2-bromo-ethylene (Z)-1-[4-(4-Diethylaminobutylamino)phenyl]-1,2-diphenyl-2-bromo-ethylene;

1,1-Bis-[4-(4-diethylaminobutoxy)phenyl]-2-phenyl-2-chloro-ethylene;

(E)-1-[4-(4-Diethylaminobutoxy)phenyl]-1-(4-hydroxy)phenyl-2-phenyl-2-chloro-ethylene;

(Z)-1-[4-(4-Diethylaminobutoxy )phenyl]-1-(4hydroxy)phenyl-2-phenyl-2-chloro-ethylene;

(E)-1-[4-(4-Diethylaminobutoxy)phenyl]-1-phenyl-2-(4-hydroxy)phenyl-2-chloro-ethylene;

(Z)-1-[4-(4-Diethylaminobutoxy)phenyl]-1-phenyl-2-(4-hydroxy)phenyl-2-chloro-ethylene;

(E)-1-[4-(4-Ethylaminobutoxy)phenyl]-1,2-diphenyl-2-chloro-ethylene;

(Z)-1-[4-(4-Ethylaminobutoxy)phenyl]-1,2-diphenyl-2-chloro-ethylene;

(E)-1-[4-(4-Methylaminobutoxy)phenyl]-1,2-diphenyl-2-chloro-ethylene;

(Z)-1-[4-(4-Methylaminobutoxy)phenyl]-1,2-diphenyl-2-chloro-ethylene;

(E)-1-[4-(4-Propylaminobutoxy)phenyl]-1,2-diphenyl-2-chloro-ethylene;

(Z)-1-[4-(4-Propylaminobutoxy)phenyl]-1,2-diphenyl-2-chloro-ethylene;

(E)-1-[4-(4-Dimethylaminobutoxy)phenyl]-1-(4-hydroxy)phenyl-2-phenyl-2-chloro-ethylene;

(Z)-1-[4-(4-Dimethylaminobutoxy)phenyl]-1-(4-hydroxy)phenyl-2-phenyl-2-chloro-ethylene;

(E)-1-[4-(4-Dipropylaminobutoxy)phenyl]-1-(4hydroxy)phenyl-2-phenyl-2-chloro-ethylene;

(Z)-1-[4-(4-Dipropylaminobutoxy)phenyl]-1-(4-hydroxy)phenyl-2-phenyl-2-chloro-ethylene;

(E)-1-[4-(4-Dimethylaminobutoxy)phenyl]-1,2-phenyl-2-phenyl-2-chloro-ethylene;

(Z)-1-[4-(4-Dimethylaminobutoxy)phenyl]-1,2-diphenyl-2-phenyl-2-chloro-ethylene;

(E)-1-[4-(4-Dipropylaminobutoxy)phenyl]-1,2-diphenyl-2-phenyl-2-chloro-ethylene;

(Z)-1-[4-(4-Dipropylaminobutoxy)phenyl]-1,2-diphenyl-2-phenyl-2-chloro-ethylene;

(E)-1-[4-(4-(Piperidin-1-yl)-butoxy)phenyl]-1,2-diphenyl-2-chloro-ethylene;

(Z)-1-[4-(4-(Piperidin-1-yl)-butoxy )phenyl]-1,2-diphenyl-2-chloro-ethylene;

(E)-1-[4-[4-(Piperazin-1-yl)-butoxy)phenyl]-1,2-diphenyl-2-chloro-ethylene;

(Z)-1-[4-[4-(Piperazin-1-yl)-butoxy)phenyl]-1,2-diphenyl-2-chloro-ethylene;

(E)-1-[4-[4-(4-Methylpiperazin-1-yl)-butoxy)phenyl]-1,2-diphenyl-2-chloro-ethylene;

(Z)-1-[4-[4-(4-Methylpiperazin-1-yl)-butoxy)phenyl]-1,2-diphenyl-2-chloro-ethylene;

(E)-1-[4-(4-(Morpholin-1-yl)-butoxy )phenyl]-1,2-diphenyl-2-chloro-ethylene;

(Z)-1-[4-(4-(Morpholin-1-yl)-butoxy )phenyl]-1,2-diphenyl-2-chloro-ethylene;

(E)-1-[4-(4-(Pyrrolidin-1-yl)-butoxy)phenyl]-1,2-diphenyl-2-chloro-ethylene;

(Z)-1-[4-(4-(Pyrrolidin-1-yl)-butoxy)phenyl]-1,2-diphenyl-2-chloro-ethylene.

The compounds of Formula I and Formula II in which Y is O can be prepared as described in Scheme A. All substituents, unless otherwise indicated, are previously defined. The reagents and starting materials are readily available to one of ordinary skill in the art.

SCHEME A

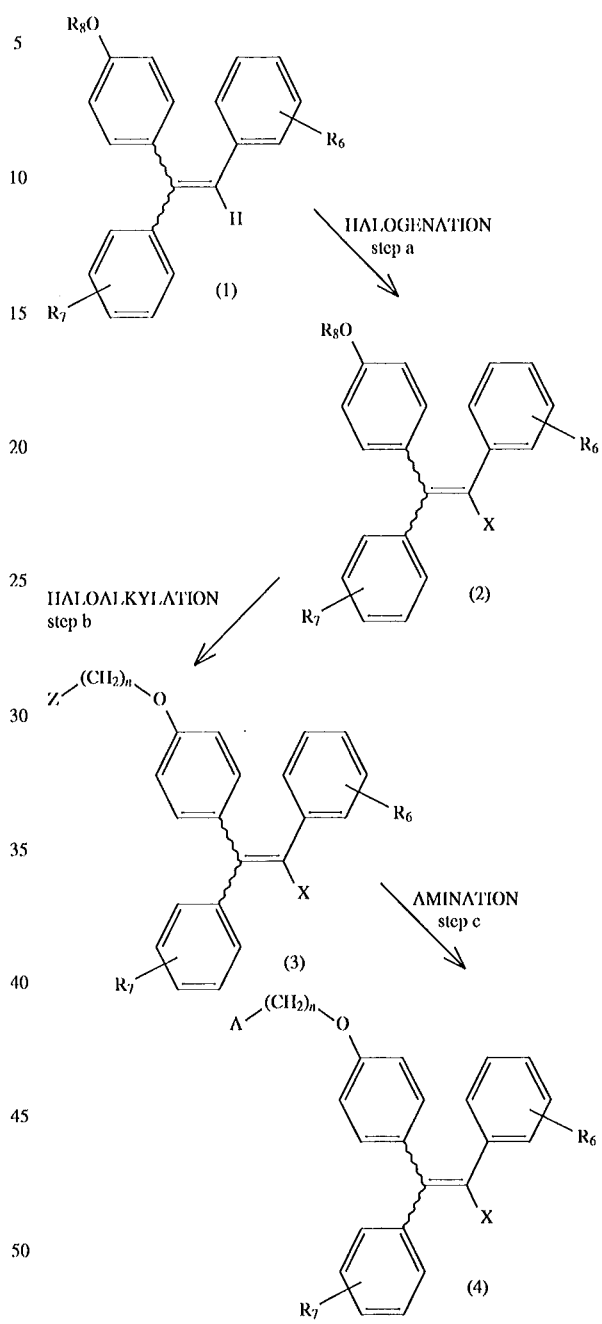

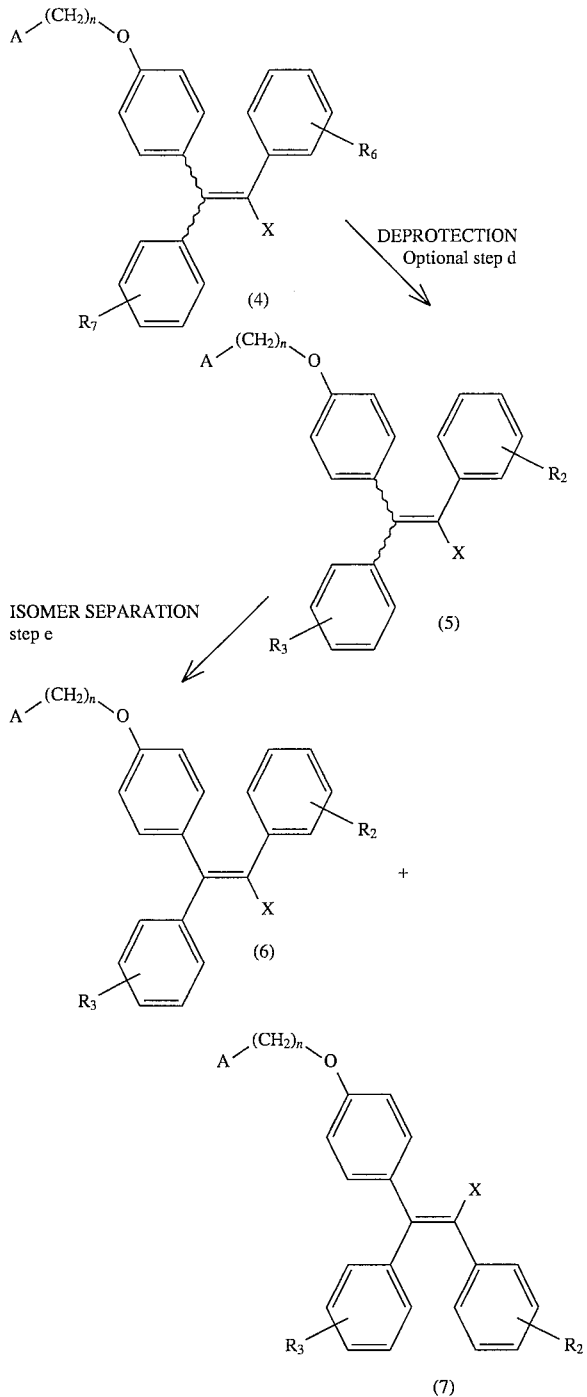

In Scheme A, step a, an appropriate triaryl-ethylene of structure 1 is chlorinated or brominated to give a halo-triaryl-ethylene of structure 2.

An appropriate triaryl-ethylene of the structure 1 is one in which $R_8$ is hydrogen or a suitable hydroxy protecting group; $R_6$ is as defined for $R_2$, or $R_6$ is a suitably protected hydroxy which after deprotection provide compounds of Formula I and Formula II in which $R_2$ is a hydroxy group; and $R_7$ is as defined for $R_3$, or $R_7$ is a suitably protected hydroxy which after deprotection provide compounds of Formula I and Formula II in which $R_3$ is a hydroxy group, or provides an intermediate for the preparation of a compound of Formula I and Formula II in which $R_3$ is $-O(CH_2)_pA_1$ wherein p=n and $A=A_1$; or $R_7$ is a suitably protected hydroxy which allows for removal in a sequential manner providing an intermediate for the preparation of compounds of Formula I and Formula II in which $R_3$ is $-O(CH_2)_pA_1$ wherein p≠n and either $A=A_1$ or $A≠A_1$, or in which $R_3$ is $-O(CH_2)_pA_1$ wherein p=n and $A≠A_1$. The selection, use, removal, and sequential removal of suitable hydroxy protecting groups, such as benzyl, p-methoxybenzyl, methyl, t-butyldimethylsilyl, and acetyl, is well known and appreciated in the art and described in *Protecting Groups in Organic synthesis* by T. Greene.

For example, an appropriate triaryl-ethylene of structure 1 is contacted with a molar excess of chlorine, bromine, N-chlorosuccinimide, or N-bromosuccinimide in a suitable solvent, such as chloroform or dichloromethane. The reaction is carried out at temperatures from ambient temperature to the reflux temperature of the solvent. After stirring for from 1–72 hours the product can be isolated and purified by techniques well known in the art. For example, the reaction mixture can be concentrated in vacuo and the product purified by chromatography on silica gel eluting with a suitable organic solvent. The material obtained can be further purified, if desired, by recrystallization from a suitable organic solvent to give a halo-triaryl-ethylene of structure 2.

As is appreciated by one of ordinary skill in the art, when a halo-triaryl-ethylene of structure 2 is derived from a triaryl-ethylene of structure 1 in which $R_8$ is a suitable hydroxy protecting group, the protecting group is removed before step b can be carried out. When a halo-triaryl-ethylene of structure 2 is derived from a triaryl-ethylene of structure 1 in which $R_8$ is a suitable protecting group and $R_7$ is a suitably protected hydroxy either the protecting groups are removed before step b is carried out or they are removed in a sequential manner. When the protecting groups are removed in a sequential manner intermediates are provided for the preparation of compounds of Formula I and Formula II in which $R_3$ is $-O(CH_2)_pA_1$ wherein p≠n and either $A=A_1$ or $A≠A_1$ and in which $R_3$ is $-O(CH_2)_pA_1$ wherein p=n and $A≠A_1$.

In Scheme A, step b, a halo-triaryl-ethylene of structure 2 is contacted with an appropriate dihaloalkane to form a ω-haloalkoxy-triaryl-ethylene of structure 3.

An appropriate dihaloalkane, $Z(CH_2)_nZ_1$, is one in which Z and $Z_1$ each may be independently a chlorine atom, a bromine atom, or a iodine atom and n is an integer from 4 to 12 and corresponds the n desired in the final product of Formula I and Formula II.

For example, a halo-triaryl-ethylene of structure 2 is contacted with a 1.1 to 10 fold molar excess of an appropriate dihaloalkane. The reaction is carried out in the presence of a suitable base, such as sodium ethoxide, sodium methoxide, potassium hydroxide, sodium hydroxide, and sodium carbonate. The reaction is carried out in a solvent, such as ethanol, methanol, tetrahydrofuran, acetonitrile, dimethylformamide, or dimethyl sulfoxide. The reaction is carried out at temperatures of from 0° C. to the refluxing temperature of the solvent. For compounds of structure 2 in which RS is hydrogen and $R_7$ is a hydroxy group the use 1.1 molar equivalents of an appropriate dihaloalkane and a suitable base allows for the preparation of a compound of Formula I and Formula II in which $R_7$ is a hydroxy group. For compounds of structure 2 in which $R_8$ is hydrogen and $R_7$ is a hydroxy group the use of from 2 to 10 molar equivalents of an appropriate dihaloalkane and a suitable base gives an bis-ω-haloalkoxy-triaryl-ethylene which is an intermediate in the production of a compound of Formula I and Formula II in which $R_3$ is —O(CH$_2$)$_p$A$_1$ wherein p=n and A=A$_1$. A ω-haloalkoxy-triaryl-ethylene of structure 3 may be isolated from the reaction zone by evaporation and extraction and may be purified by methods well known in the art, such as chromatography and recrystallization.

In Scheme A, step c, ω-haloalkoxy-triaryl-ethylene of structure 3 is contacted with an appropriate amine, HNRR$_1$, in which R and R$_1$ are as defined above, morpholine, piperidine, piperazine, 4-methylpiperazine, or pyrrolidine to give ω-aminoalkoxy-triaryl-ethylene of structure 4.

For example, ω-haloalkoxy-triaryl-ethylene of structure 2 is contacted with a large molar excess of an appropriate amine in a solvent, such as ethanol, methanol, water, ethanol/water mixtures, or methanol/water mixtures. A large molar excess of amine is used so that the amine can also acts as a base to take up the acid liberated in the reaction. The reaction may be carried out in the presence of a suitable catalyst, such as potassium iodide. The reaction vessel may be sealed to prevent the escape of volatile amines. The reaction mixture is heated to temperatures of from 40° C. to 100° C. For compounds of structure 3 in which $R_7$ is a ω-haloalkoxy group the use of an additional portion of an appropriate amine gives a bis-ω-aminoalkoxy-triaryl-ethylene which is a compound of Formula I and Formula II in which $R_3$ is —O(CH$_2$)$_p$A$_1$ wherein p=n and A=A$_1$. The product can be isolated and purified by techniques well known in the art. For example, the reaction mixture can be concentrated in vacuo and the product purified by techniques well known in the art, such as salt formation, chromatography eluting with a suitable solvent, or recrystallization from a suitable organic solvent.

In Scheme A, step a, may be carried out before or after steps b and c are carried out.

In Scheme A, Optional step d, for a ω-aminoalkoxy-triaryl-ethylene of structure 4 in which $R_6$ or $R_7$ is a protected hydroxy group may be deprotected to provide ω-aminoalkoxy-triaryl-ethylene of structure 5 in which either, $R_2$ or $R_3$, or $R_2$ and $R_3$, are hydroxy as desired in the final product of Formula I and Formula II. As is appreciated by one skilled in the art the compounds of Formula I and Formula II in which $R_3$ is hydroxy can be, by sequentially performing the steps of Scheme A, used as intermediates for preparing compounds of Formula I and Formula II in which $R_3$ is —O(CH$_2$)$_p$A$_1$ wherein p≠n and either A=A$_1$ or A≠A$_1$ or in which $R_3$ is —O(CH$_2$)$_p$A$_1$ wherein p=n and A≠A$_1$.

The selection, use, removal, and sequential removal of suitable hydroxy protecting groups is well known and appreciated in the art and described in *Protecting Groups in Organic Synthesis* by T. Greene.

In Scheme A, step e, the isomers of a Ω-aminoalkoxy-triaryl-ethylene of structure 4 or 5 can be separated to give a (E)-ω-aminoalkoxy-triaryl-ethylene of structure 4 or 5 and the (Z)-ω-aminoalkoxy-triaryl-ethylene of structure 4 or 5.

For example, the isomers of compounds of structure 5 can be separated and purified by high-performance liquid chromatography or recrystallization of salt to give a (E)-ω-aminoalkoxy-triaryl-ethylene and a (Z)-ω-aminoalkoxy-triaryl-ethylene.

Pharmaceutically acceptable salts of a (E)-ω-aminoalkoxy-triaryl-ethylene of or of a (Z)-ω-aminoalkoxy-triaryl-ethylene can be formed in an additional step as is well known and practiced in the art.

The following examples present typical syntheses as described in Scheme A. These examples are understood to be illustrative only and are not intended to limit the scope of the invention in any way. As used in the following examples, the following terms have the meanings indicated: "g" refers to grams, "mg" refers to milligrams, "mmol" refers to millimoles, "mL" refers to milliliters, "°C" refers to degrees Celsius, "R$_f$" refers to retention factor, "mp" refers to melting point, "HPLC" refers to high performance liquid chromatography.

EXAMPLE 1

(E and Z)-1-[(4-Hydroxy)phenyl]-1,2-diphenyl,2-chloro-ethylene

Combine (E and Z)-1-[(4-hydroxy)phenyl]-1,2-diphenyl-ethylene [Cacchi et al, Tet. Lets. 25, 3137–3140 (1984)] (0.90 g, 3.31 mmol) and N-chlorosuccinimide (0.486 g, 3.64 mmol) in chloroform (20 mL). Heat to reflux and allow to stir at reflux for 48 hours. Evaporate in vacuo. Chromatograph on silica gel eluting with 20% ethyl acetate/hexane to give the title compound as a solid: mp; 127°–129° C.

EXAMPLE 2

(E and Z)-1-[4,-(4-Chlorobutoxy)phenyl]-1,2-diphenyl-2-chloro-ethylene

Combine (E and Z)-1-[(4-hydroxy)phenyl]-1,2-diphenyl-2-chloro-ethylene (15.0 g, 49.0 mmol) and 4-bromo-1-chlorobutane (35 g, 200 mmol) in ethanol (250 mL). Add sodium methoxide (2.75 g, 50.0 mmol). Heat to reflux under an inert atmosphere. After 5 hours concentrate on a steam bath to obtain a residue. Partition the residue between diethyl ether and 10% sodium hydroxide. Separate the layers and dry the organic layer over MgSO$_4$, filter, and evaporate in vacuo to give the title compound which is taken on to the next step without further purification.

EXAMPLE 3

(E and Z)-1-[4-(4-Diethylaminobutoxy)phenyl]-1,2-diphenyl-2-chloro-ethylene

Combine (E and Z)-1-[4-(4-chlorobutoxy)phenyl]-1,2-diphenyl-2-chloro-ethylene (19.0 g, 47.8 mmol), diethylamine (20 mL, 193 mmol), and ethanol (100 mL). Seal in a reaction vessel and heat to 80° C. for 48 hours. Cool to ambient temperature and carefully open the pressure vessel. Concentrate in vacuo to obtain a residue. Dissolve the residue in butanone and add citric acid (9.0 g, 47 mmol). Filter to give a mixture of the isomers as their citric acid salts. Dissolve (E and Z)-1-[4-(4diethylaminobutoxy)phenyl]-1,2-diphenyl-2-chloro-ethylene citric acid salts (1.5 g) in 1/1 acetonitrile/water and adjust the pH to 9 with 2 M aqueous sodium hydroxide. Extract with chloroform and evaporate to give a mixture of the isomers as a residue. Separate the isomers by HPLC, 90 mg per injection, using a Waters and Associates μPorasil column (19 mm by 300 mm), eluting with 80/20/0.2 chloroform/hexane/triethylamine at 15 mL/minute to give (Z)-1-[4-(4-diethylaminobutoxy)phenyl]- 1,2-diphenyl-2-chloro-ethylene and (E)-1-[4-(4-diethylaminobutoxy)phenyl]-1,2-diphenyl-2-chloro-ethylene.

EXAMPLE 4

(E)-1-[4-(4-Diethylaminobutoxy) phenyl]-1,2-diphenyl-2-chloro-ethylene citrate salt

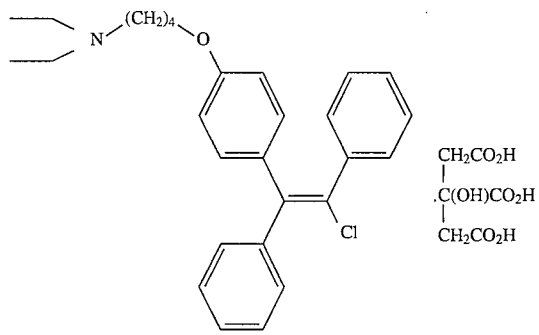

Combine citric acid (164.7 mg, 0.86 mmol) and ethanol mL) and heat until the solid dissolves. Combine (Z)-1-[4-(4-diethylaminobutoxy)phenyl]-1,2-diphenyl- 2-chloro-ethylene (372.6 mg, 0.86 mmol) and warm ethanol (3 mL) and add with stirring to the citric acid solution prepared above. Cool to 4° C. and allow to stand for 18 hours. Filter to give the title compound as a solid: mp; 127°–130° C.

EXAMPLE 5

(Z)-1-[4-(4-Diethylaminobutoxy)phenyl]-1,2-diphenyl-2-chloro-ethylene citrate salt

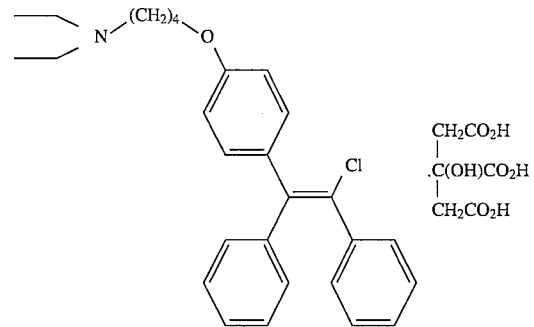

Combine citric acid (167.6 mg, 0.87 mmol) and ethanol (3 mL) and heat until the solid dissolves. Combine (Z)-1-[4-(4-diethylaminobutoxy)phenyl]- 1,2-diphenyl-2-chloro-ethylene (378.7 mg, 0.87 mmol) and warm ethanol (3 mL) and add with stirring to the citric acid solution prepared above. Cool to 4° C. and allow to stand for 18 hours. Filter to give the title compound as a solid: mp; 150°–151° C.

EXAMPLE 6

(E and Z )-1-[4-(4-Ethylaminobutoxy)phenyl]-1,2-diphenyl-2-chloro-ethylene citrate salt

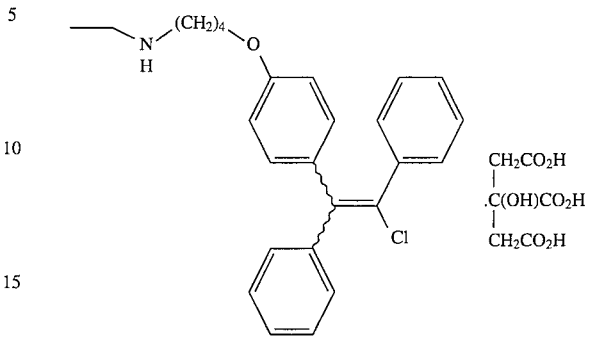

Combine (E and Z)-1-[4-(4-chlorobutoxy)phenyl]-1,2-diphenyl-2-chloro-ethylene (1.0 g, 2.5 mmol), ethylamine (15 mL, 193 mmol), potassium iodide (0.200 g), ethanol (2 mL), and water (5 mL). Heat to a gentle reflux. After 24 hours, cool to ambient temperature and concentrate in vacuo to obtain a residue. Chromatograph on silica gel eluting with 7% methanol/dichloromethane to obtain a residue. Combine the residue and butanone (6 mL). Add citric acid (0.52 g, 2.7 mmol) dissolved in butanone (4 mL). Allow to slowly evaporate until a solid forms, filter, and dry in vacuo to give the title compound.

EXAMPLE 7

(E and Z)-1-[4-(4-(Piperidin-1-yl)-butoxy)phenyl]-1,2-diphenyl-2-chloro-ethylene citrate salt Combine (E and Z)-1-[4-(4-chlorobutoxy)phenyl]-1,2-diphenyl-2-chloro-ethylene (1.0 g, 2.5 mmol), piperidine (7.5 g), potassium iodide (0.200 g) and water (5 mL). Heat to 80° C. After 18 hours, cool to ambient temperature and partition the reaction mixture between water and ethyl acetate. Separate the organic layer and extract 3 times

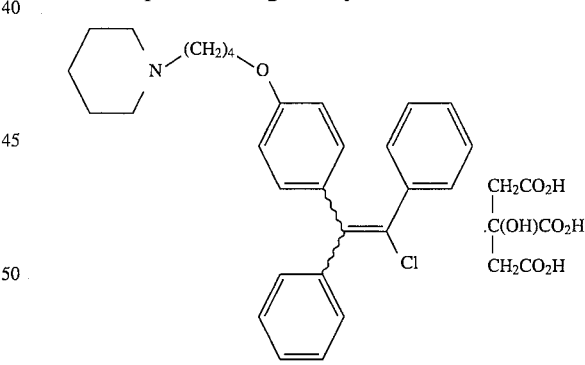

with water. Dry the organic layer over MgSO$_4$ and evaporate in vacuo. Chromatograph on silica gel eluting with 6% methanol/dichloromethane to obtain a residue (1.01 g). Combine the residue and butanone (6 mL). Add citric acid (0.423 g, 2.2 mmol) dissolved in butanone (2 mL). Evaporate in vacuo to give the title compound.

EXAMPLE 8

(E and Z)-1-[4-[4-(4-Methylpiperazin-1-yl)-butoxy]phenyl]-1,2-diphenyl-2-chloro-ethylene citrate salt

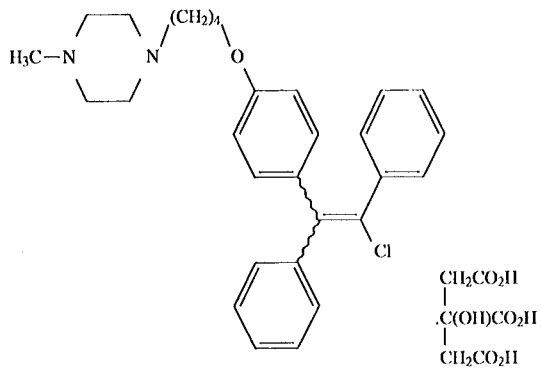

Combine (E and Z)-1-[4-(4-chlorobutoxy)phenyl]-1,2-diphenyl-2-chloro-ethylene (1.0 g, 2.5 mmol), 4-methylpiperazine (5 mL), potassium iodide (0.200 g), and water (3 mL). Heat to 80° C. After 18 hours, cool to ambient temperature and partition the reaction mixture between water and ethyl acetate. Separate the organic layer and extract 3 times with water. Dry the organic layer over $MgSO_4$ and evaporate in vacuo. Chromatograph on silica gel eluting with 5% methanol/dichloromethane to obtain a residue (0.758 g). Combine the residue and butanone (4 mL). Add citric acid (0.307 g, 1.6 mmol) dissolved in butanone (2 mL). Allow to slowly evaporate until a solid forms, filter, and dry in vacuo to give the title compound.

EXAMPLE 9

(E and Z)-1-[4-(4-(pyrrolidin-1-yl)-butoxy)phenyl]-1,2-diphenyl-2-chloro-ethylene citrate salt

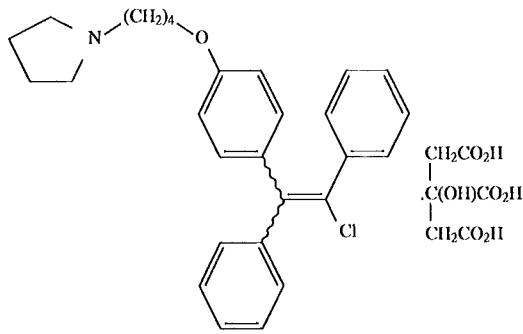

Combine (E and Z)-1-[4-(4-chlorobutoxy)phenyl]-1,2-diphenyl-2-chloro-ethylene (0.9 g, 2.25 mmol), pyrrolidine (5 mL), potassium iodide (0.200 g), and water (5 mL). Heat to 80° C. After 18 hours, cool to ambient temperature and partition the reaction mixture between water and ethyl acetate. Separate the organic layer and extract 3 times with water. Dry the organic layer over $MgSO_4$ and evaporate in vacuo. Chromatograph on silica gel eluting with 6% methanol/dichloromethane to obtain a residue (0.499 g). Combine the residue and butanone (2 mL). Add citric acid (0.211 g, 1.1 mmol) dissolved in butanone (2 mL). Allow to slowly evaporate until a solid forms, filter, and dry in vacuo to give the title compound.

EXAMPLE 10

(E and Z)-1-[4-(5-Chloropentoxy)phenyl]-1,2-diphenyl-2-chloro-ethylene

Combine (E and Z)-1-[(4-hydroxy)phenyl]-1,2-diphenyl-2-chloro-ethylene (2.3 g, 7.5 mmol) and 5-bromo-1-chloropentane (2.78 g, 15.0 mmol) in ethanol (40 mL). Add a solution of sodium ethoxide in ethanol (11.12 mL, 0.67 M, 7.5 mmol). Heat to reflux under an inert atmosphere. After 24 hours concentrate in vacuo. Chromatograph on silica gel eluting with ½ ethyl acetate/hexane. Concentration of the product containing fractions to give the title compound which is taken on to the next step without further purification.

EXAMPLE 11

(E and Z)-1-[4-(5-Diethylaminopentoxy)phenyl]-1,2-diphenyl-2-chloro-ethylene

Combine (E and Z)-1-[4-(5-chloropentoxy)phenyl]-1,2-diphenyl-2-chloro-ethylene (3.08 g, 7.5 mmol), diethylamine (5.5 g, 75.0 mmol) and potassium iodide (30 mg, 0.178 mmol) in water (8.0 mL). Heat to 40° C. for 4 hours and then cool to ambient temperature and allow to stand for 72 hours. Add diethylamine (10 mL) and heat to 80° C. After 3 hours chromatograph on silica gel eluting first with 20% ethyl acetate/hexane and then with 20% ethyl acetate/hexane containing 5% triethylamine. Combine product containing fractions and concentrate in vacuo. Chromatograph, again, on silica gel eluting with 7% methanol/dichloromethane. Concentration of product containing fractions to give a mixture of the isomers as a residue. Separate the isomers by HPLC, 90 mg per injection, using a Waters and Associates µPorasil column (19 mm by 300 mm), eluting with 80/20/0.2 chloroform/hexane/triethylamine at 20 mL/minute to give (E)-1-[4-(5-diethylaminopentoxy)phenyl]- 1,2-diphenyl-2-chloro-ethylene and (Z)-1-[4-(5-diethylaminopentoxy)phenyl]-1,2-diphenyl-2-chloro-ethylene.

EXAMPLE 12

(E)-1-[4-(5-Diethylaminopentoxy)phenyl]-1,2-diphenyl-2-chloro-ethylene citrate salt

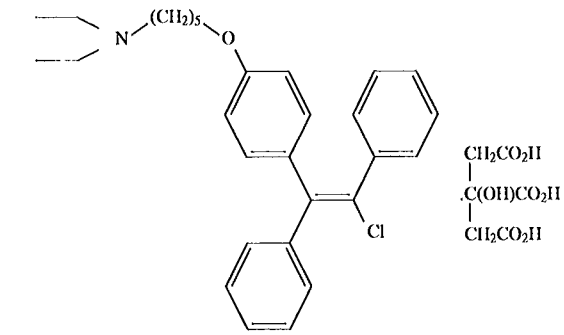

Combine citric acid (192.13 mg, 1.21 mmol) and isopropanol (3 mL) and heat until the solid dissolves. Combine (E)-1-[4-(5-diethylaminopentoxy)phenyl]-1,2-diphenyl-2-chloro-ethylene (543.2 mg, 1.21 mmol) and warm isopropanol (3 mL) and add with stirring to the citric acid solution prepared above. Filter while still warm and then cool in a freezer at −20° C. until crystals begin to form and then allow to stand at ambient temperature for 18 hours. Filter to give the title compound as a solid: mp; 124°–127° C.

EXAMPLE 13

(Z)-1-[4-(5-Diethylaminopentoxy)phenyl]-1,2-diphenyl-2-chloro-ethylene citrate salt

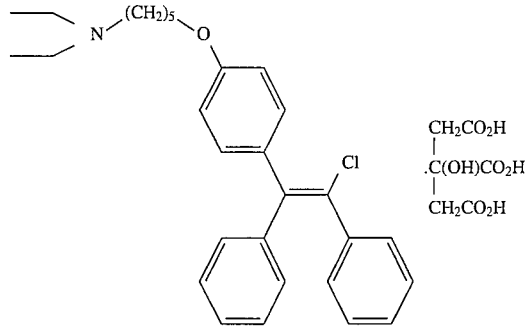

Combine citric acid (192.13 mg, 1.21 mmol) and isopropanol (3 mL) and heat until the solid dissolves. Combine (Z)-1-[4-(5-diethylaminopentoxy)phenyl]-1,2-diphenyl-2-chloro-ethylene (543.2 mg, 1.21 mmol) and warm isopropanol (3 mL) and add with stirring to the citric acid solution prepared above. Filter while still warm and then cool in a freezer at −20° C. until crystals begin to form and then allow to stand at ambient temperature for 18 hours. Filter to give the title compound as a solid: mp; 124°–127° C.

EXAMPLE 14

1,1-Bis-(4-methoxy)phenyl-2-phenyl-ethanol

Combine benzyl magnesium chloride (180 mL, 2 M in tetrahydrofuran, 360 mmol) and 4,4'-dimethoxybenzophenone (50 g, 207 mmol), Heat to a gentle reflux. After 72 hours, carefully pour the reaction mixture onto a mixture of ice (300 g) and a saturated aqueous solution of ammonium chloride (50 mL). Extract with diethyl ether, dry the organic layer over $MgSO_4$, and evaporate in vacuo to give the title compound.

EXAMPLE 15

1,1-Bis-(4-methoxy)phenyl-2-phenyl-ethylene

Combine 1,1-bis-(4-methoxy)phenyl-2-phenyl-ethanol obtained in Example 14 and 12M hydrochloric acid (50 mL) is ethanol (400 mL). Heat to reflux. After 24 hours, cool the reaction mixture to ambient temperature. Evaporate in vacuo to obtain a reside. Partition the residue between water and ethyl acetate. Separate the organic layer, dry over the $MgSO_4$, and evaporate in vacuo to give the title compound.

EXAMPLE 16

1,1-Bis-(4-methoxy)phenyl-2-phenyl-2-phenyl-2-chloro-ethylene

Combine 1,1-bis-(4-methoxy)phenyl-2-phenyl-ethylene (24 g, 75.8 mmol) and N-chlorosuccinimide (10.7 g, 80 mmol) in chloroform (100 mL). Heat to 60° C. After 18 hours, cool to ambient temperature and evaporate in vacuo. Chromatograph on silica gel eluting with 1/10 ethyl acetate/hexane to give the title compound.

EXAMPLE 17

1,1-Bis-(4-hydroxy)-phenyl-2-phenyl-2-chloro-ethylene

Heat pyridinium hydrochloride (140 g, 1210 mmol) to 220° C. Add portionwise, 1,1-bis-(4-methoxy)phenyl-2-phenyl-2-chloro-ethylene (37.5 g, 107 mmol) and maintain the temperature at 220° C. After 45 minutes, pour the reaction mixture onto ice (400 g). Extract with ethyl acetate. The organic layer is extracted with water and 0.5 M hydrochloric acid solution. Separate the organic layer, dry over the $MgSO_4$, and evaporate in vacuo to give the title compound.

EXAMPLE 18

(E and Z)-1-[4-(4-Chlorobutoxy)phenyl]-1-(4-hydroxy)phenyl-2-phenyl-2-chloro-ethylene and 1,1-Bis-[4-(4-chlorobutoxy)phenyl]-2-phenyl-2-chloro-ethylene Add sodium metal (0.440 g, 19 mmol) and ethanol (80 mL) and stir until the sodium metal has reacted. Add 1,1-bis-(4-hydroxy)phenyl-2-phenyl-2-chloro-ethylene (5.56 g, 17.2 mmol) and heat the reaction mixture to 40° C. for 15 minutes. Add 1-bromo-4-chlorobutane (0.34 g, 20 mmol) and heat to a gentle reflux. After 72 hours, evaporate in vacuo. Chromatograph on silica gel eluting with dichloromethane to give (E and Z)-1-[4-(4-chlorobutoxy)phenyl]-1-(4-hydroxy)phenyl-2-phenyl-2-chloro-ethylene (2.5 g) and 1,1-bis-[4-(4-chlorobutoxy)phenyl]-2-phenyl-2-chloro-ethylene (0.96 g).

EXAMPLE 19

(E and Z)-1-[4-(4-Diethylaminobutoxy)phenyl]-1-(4-hydroxy)phenyl-2-phenyl-2-chloro-ethylene citrate salt Combine (E and Z)-1-[4-(4-chlorobutoxy)phenyl]-1-(4-hydroxy)phenyl-2-phenyl-2-chloro-ethylene (2.5 g, 6 mmol), diethylamine (50 mL), potassium iodide (0.50 g), and water (50 mL). Heat to a gentle reflux. After 16 hours, cool the reaction mixture to ambient temperature. Partition the reaction mixture between water and ethyl acetate. Separate the organic layer, dry over $MgSO_4$, and evaporate Chromatograph on silica gel eluting with 15% methanol/dichloromethane to give a residue. Combine the residue and chloroform (50 mL). Divide the chloroform solution in half Evaporate one half in vacuo to obtain a residue. Combine the residue obtained from the chloroform solution and butanone (7 mL). Add citric acid (0.345 g) dissolved in butanone (4 mL) and methanol (1 mL). Allow to stand until a solid forms, collect by filtration and dry in vacuo to give the title compound. Evaporate one half in vacuo to obtain a residue for separation of the isomers on HPLC.

Separate the isomers by HPLC, 20 mg per injection, using a 5 μm Spherisorb CN (column #61037) (21.2 mm by 250 mm), eluting with 55/40/5 chloroform/hexane/methanol containing 0.05% triethylamine at 20 mL/minute to give (E)-1-[4-(4-diethylaminobutoxy)phenyl]-1-(4-hydroxy)phenyl-2-phenyl-2-chloro-ethylene and (Z)-1-[4-(4diethylaminobutoxy)phenyl]-1-(4-hydroxy)phenyl-2-phenyl-2-chloro-ethylene.

EXAMPLE 20

(E)-1-[4-(4-Diethylaminobutoxy)phenyl]-1-(4-hydroxy)phenyl-2-phenyl-2-chloro-ethylene citrate salt

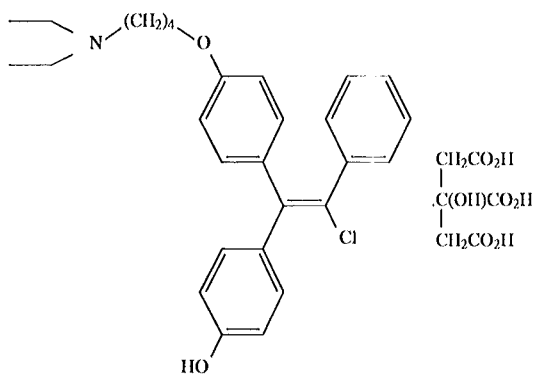

Combine citric acid (48 mg, 0.25 mmol) and butanone (10 mL). Combine (E)-1-[4-(4-diethylaminobutoxy)phenyl]-1-(4-hydroxy)phenyl- 2-phenyl-2-chloro-ethylene (115 mg, 0.26 mmol). Allow to stand until a solid forms, filter to give the title compound as a solid: mp; 94°–96° C.

EXAMPLE 21

(Z)-1-[4-(4-Diethylaminobutoxy)phenyl]-1-(4-hydroxy)phenyl-2-phenyl-2-chloro-ethylene citrate salt

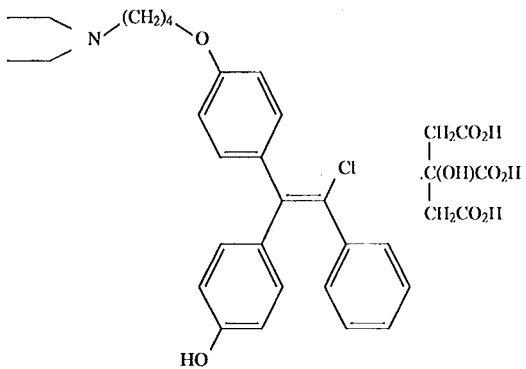

Combine citric acid (48 mg, 0.25 mmol) and butanone (10 mL). Combine (E)-1-[4-(4-diethylaminobutoxy)phenyl]-1-(4-hydroxy)phenyl- 2-phenyl-2-chloro-ethylene (118 mg, 0.26 mmol). Allow to stand until a solid forms, filter to give the title compound as a solid: mp; 90°–92° C.

EXAMPLE 22

1,1-Bis-[4-(4-diethylaminobutoxy)phenyl]-2-phenyl-2-chloro-ethylene

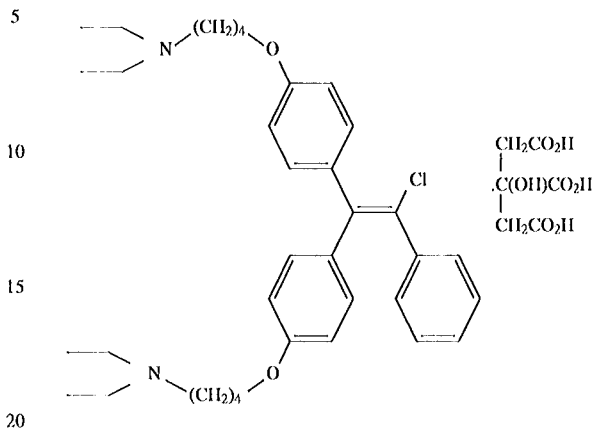

Combine 1,1-bis-[4-(4-chlorobutoxy)phenyl]-2-phenyl-2-chloro-ethylene (0.950 g, 1.89 mmol), diethylamine (15 mL), potassium iodide (0.10 g), ethanol (5 mL), and water (15 mL). Heat to a gentle reflux. After 8 hours, cool the reaction mixture to ambient temperature. Partition the reaction mixture between water and ethyl acetate. Separate the organic layer, dry over the $MgSO_4$, and evaporate in vacuo. Chromatograph on silica gel eluting with 20% methanol/dichloromethane to give a residue. Combine the residue and butanone (5 mL). Add citric acid (0.110 g) dissolved in butanone (5 mL). Heat and add methanol until dissolution. Allow to slowly evaporate until a solid forms, collect by filtration and dry in vacuo to give the title compound.

Alternately, the compounds of Formula I and Formula II in which Y is O can be prepared as described in Scheme B. All substituents, unless otherwise indicated, are previously defined. The reagents and starting materials are readily available to one of ordinary skill in the art.

SCHEME B

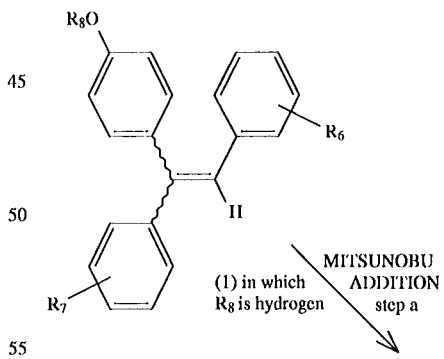

-continued
SCHEME B

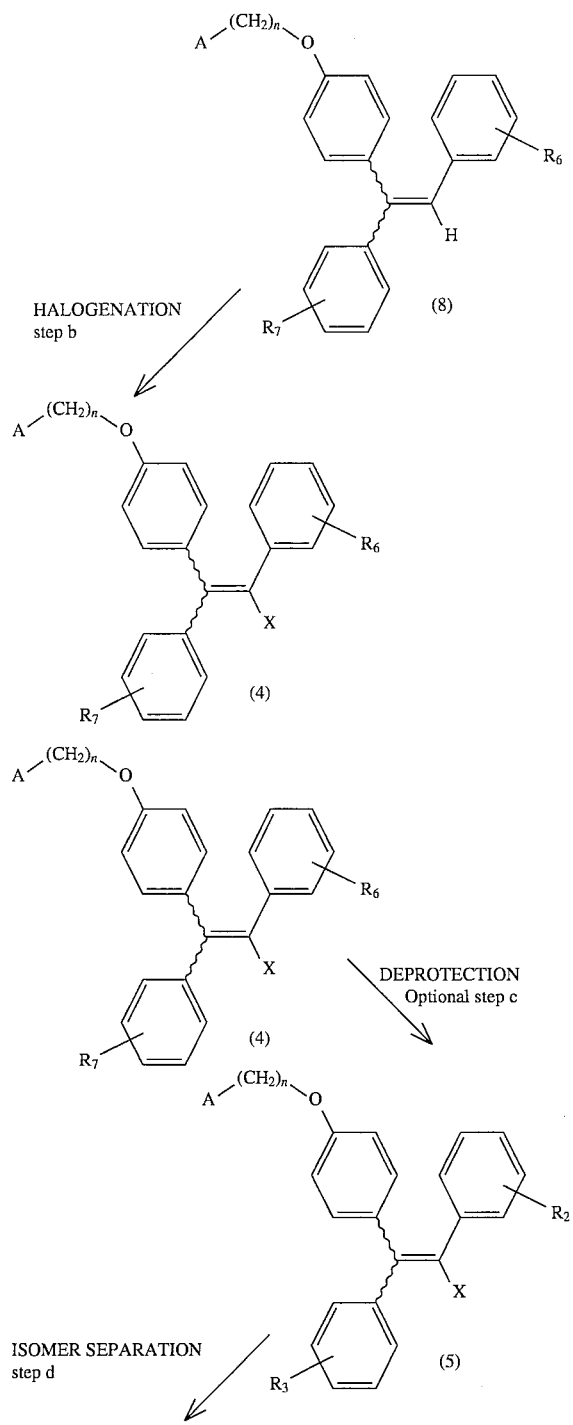

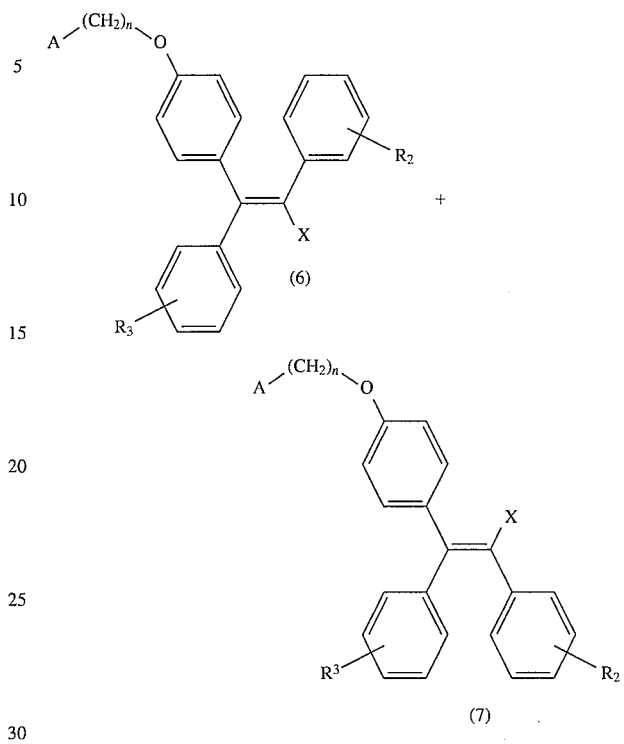

In Scheme B, step a, an appropriate ω-aminoalcohol is added by a Mitsunobu addition to an appropriate triarylethylene of structure 1 in which $R_8$ is hydrogen to give a ω-aminoalkoxy-triaryl-ethylene of structure 8.

An appropriate ω-aminoalcohol, HO—$(CH_2)_n$—A, is one in which A and n are as defined above and are as desired in the final product of Formula I and Formula II. An appropriate triaryl-ethylene of the structure 1 is one in which $R_8$ is hydrogen; $R_6$ is as defined for $R_2$, or $R_6$ is a suitably protected hydroxy which after deprotection provide compounds of Formula I and Formula II in which $R_2$ is a hydroxy group; and $R_7$ is as defined for $R_3$, or $R_7$ is a suitably protected hydroxy which after deprotection provide compounds of Formula I and Formula II in which $R_3$ is a hydroxy group, or provides an intermediate for the preparation of a compound of Formula I and Formula II in which $R_3$ is —$O(CH_2)_p A_1$ wherein p=n and A=$A_1$; or $R_7$ is a suitably protected hydroxy which allows for removal in a sequential manner providing an intermediate for the preparation of compounds of Formula I and Formula II in which $R_3$ is —$O(CH_2)_p A_1$ wherein p≠n and either A=$A_1$ or A≠$A_1$, or in which $R_3$ is —$O(CH_2)_p A_1$ wherein p=n and A≠$A_1$. The selection, use, removal, and sequential removal of suitable hydroxy protecting groups, such as benzyl, p-methoxybenzyl, methyl, t-butyldimethylsilyl, and acetyl, is well known and appreciated in the art and described in *Protecting Groups in Organic Synthesis* by T. Greene.

For example, an appropriate ω-aminoalcohol is contacted with a molar equivalent of a triaryl-ethylene of structure 1 in which $R_8$ is hydrogen and a molar equivalent of triphenylphosphine in a suitable solvent, such as tetrahydrofuran (THF). Diethyl azodicarboxylate neat or as a solution in a suitable solvent, such as tetrahydrofuran is added. After stirring for from 1–72 hours the product can be isolated and purified by techniques well known in the art. For the preparation of compounds of Formula I and Formula II in which $R_3$ is $-O(CH_2)_pA_1$ wherein p=n and A=$A_1$ a compound in which $R_7$ is hydroxy is used along with an additional equivalent of an appropriate ω-aminoalcohol, triphenylphosphine, and diethyl azodicarboxylate are used. The reaction mixture can be concentrated in vacuo to give a residue. The residue can be chromatographed on silica gel using a suitable organic eluent. The material obtained from chromatography can be recrystallized to give a ω-aminoalkoxy-triaryl-ethylene of structure 8.

In Scheme B, step b, a ω-aminoalkoxy-triaryl-ethylene of structure 8 is chlorinated or brominated to give a ω-aminoalkoxy-triaryl-ethylene of structure 4.

For example, a ω-aminoalkoxy-triaryl-ethylene of structure 8 is contacted with a molar excess of chlorine, bromine, N-chlorosuccinimide, or N-bromosuccinimide in a suitable solvent, such as chloroform or dichloromethane. The reaction is carried out at temperatures from ambient temperature to the reflux temperature of the solvent. After stirring for from 1214 72 hours the product can be isolated and purified by techniques well known in the art. For example, the reaction mixture can be concentrated in vacuo and the product purified by techniques well known in the art, such as salt formation, chromatography eluting with a suitable solvent, or recrystallization from a suitable organic solvent.

In Scheme B, steps a and b, can be carried out in any order.

In Scheme B, Optional step c, for a ω-aminoalkoxy-triaryl-ethylene of structure 4 in which $R_6$ or $R_7$ are a protected hydroxy group the protecting group is removed in a deprotection step to provide a ω-aminoalkoxy-triaryl-ethylene of structure 5 in which either, $R_2$ or $R_3$, or $R_2$ and $R_3$, are hydroxy as desired in the final product of Formula I and Formula II. The production of a compound of Formula I and II in which $R_3$ is $-O(CH_2)_pA_1$ wherein p≠n and either A=$A_1$ or A≠$A_1$ or in which $R_3$ is $-O(CH_2)_pA_1$ wherein p=n and either A=$A_1$ or A≠$A_1$ may require the removal of protecting groups in a sequential manner to provide a compound of the structure 4 in which $R_7$ is a hydroxy group. As is apparent to one skilled in the art a compound of the structure 4 in which $R_7$ is a hydroxy group can be subjected to steps b and c of Scheme A or step a of Scheme B to give a bis-ω-aminoalkoxy-triaryl-ethylene compound of Formula I and II in which $R_3$ is $-O(CH_2)_pA_1$ wherein p≠n and either A=$A_1$ or A≠$A_1$ or in which $R_3$ is $-O(CH2)_pA_1$ wherein p=n and A≠$A_1$ or a bis-ω-aminoalkoxy-triaryl-ethylene compound of Formula I and II wherein p=n and A=$A_1$.

The selection, use, removal, and sequential removal of suitable hydroxy protecting groups, such as benzyl, p-methoxybenzyl, methyl, t-butyldimethylsilyl, and acetyl, is well known and appreciated in the art and described in *Protecting Groups in Organic Synthesis* by T. Greene.

In Scheme B step d, the isomers of a ω-aminoalkoxy-triaryl-ethylene of structure 4 or 5 are separated to give the (E)-ω-aminoalkoxy-triaryl-ethylene and the (Z)-ω-aminoalkoxy-triaryl-ethylene as taught in Scheme A step c.

Pharmaceutically acceptable salts of a (E)-ω-aminoalkoxy-triaryl-ethylene or a (Z)-ω-aminoalkoxy-triaryl-ethylene can be formed in an additional step as is well known and practiced in the art.

The following examples present typical syntheses as described in Scheme B. These examples are understood to be illustrative only and are not intended to limit the scope of the invention in any way. As used in the following examples, the following terms have the meanings indicated: "g" refers to grams, "mg" refers to milligrams, "mmol" refers to millimoles, "mL" refers to milliliters, "°C." refers to degrees Celsius, "mp" refers to melting point, "HPLC" refers to high performance liquid chromatography.

EXAMPLE 23

(E and Z)-1-[4-(6-Diethylaminohexoxy)phenyl]-1,2-diphenylethylene

Combine (E and Z)-1-[(4-hydroxy))phenyl]-1,2-diphenylethylene (3.05 g, 11.2 mmol), 6-diethylaminohexanol (2.0 g, 11.5 mmol), and triphenylphosphine (3.73 g, 14.2 mmol) in THF (25 mL). Add dropwise diethyl azodicarboxylate (2.24 mL, 14.2 mmol). Stir for 24 hours. Concentrate in vacuo. Chromatograph on silica gel eluting with 7% methanol/dichloromethane. Concentration of the product containing fractions to give the title compound.

EXAMPLE 24

(E and Z)-1-[4-(6-Diethylaminohexoxy)phenyl]-1,2-diphenyl-2-chloro-ethylene

Combine (E and Z)-1-[4-(6-diethylaminohexoxy)phenyl]-1,2-diphenyl-ethylene (2.17 g, 5.07 mmol), N-chlorosuccinimide (0.745 g, 5.57 mmol), and chloroform (40 mL). Heat to reflux for 18 hours. Cool to ambient temperature. Add N-chlorosuccinimide (0.745 g, 5.57 mmol). Heat to reflux. After 2 hours evaporate Chromatograph on silica gel eluting with 10% methanol/dichloromethane. Combine product containing fractions and concentrate in vacuo to give the title compound. Separate the isomers by HPLC, 90 mg per injection, using a Waters and Associates μPorasil column (19 mm by 300 mm), eluting with 80/20/0.2 chloroform/hexane/triethylamine at 20 mL/minute to give (E)-1-[4-(6-diethylaminohexoxy)phenyl]-1,2-diphenyl-2-chloro-ethylene and (Z)-1-[4-(6-diethylaminohexoxy)phenyl]-1,2-diphenyl-2-chloro-ethylene.

EXAMPLE 25

(E)-1-[4-(6-Diethylaminohexoxy)phenyl]-1,2-diphenyl-2-chloro-ethylene citrate salt

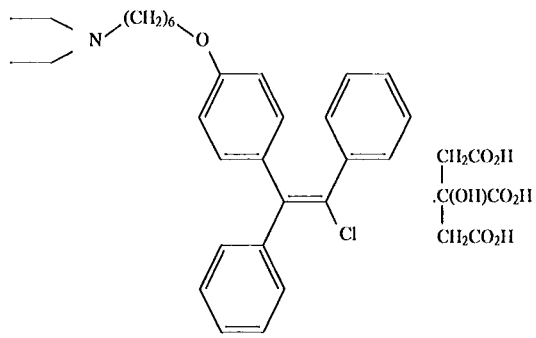

Combine citric acid (370 mg, 0.80 mmol) and ethanol (4 mL) and heat until the solid dissolves. Combine (E)-1-[4-(6-diethylaminohexoxy)phenyl]-1,2-diphenyl-2-chloro-ethylene (154 mg, 0.80 mmol) and warm ethanol (5 mL) and add with stirring to the citric acid solution prepared above. Filter while still warm and then cool in a freezer at −20° C. until crystals begin to form and then allow to stand at ambient temperature for 18 hours. Filter to give the title compound as a solid: mp; 84°–87° C.

EXAMPLE 26

(Z)-1-[4-(6-Diethylaminohexoxy)phenyl]-1,2-diphenyl-2-chloro-ethylene citrate salt

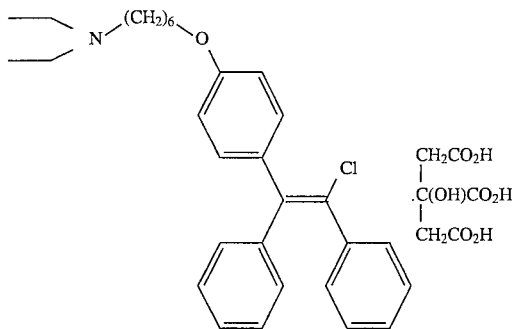

Combine citric acid (56 mg, 0.29 mmol) and ethanol (2 mL) and heat until the solid dissolves. Combine (Z)-1-[4-(6-diethylaminohexoxy)phenyl]-1,2-diphenyl-2-chloro-ethylene (134 mg, 0.29 mmol) and warm ethanol (3 mL) and add with stirring to the citric acid solution prepared above. Filter while still warm and then cool in a freezer at −20° C. until crystals begin to form and then allow to stand at ambient temperature for 18 hours. Filter to give the title compound as a solid: mp; 84°–87° C.

EXAMPLE 27

(E and Z)-1-[4-(7-Diethylaminoheptoxy)phenyl]-1,2-diphenyl-2-chloro-ethylene

Prepare by the methods taught in Example 23, using 7-diethylaminoheptanol, and Example 24 to give the title compound. Separate the isomers by HPLC, using multiple injections, using a Waters and Associates µPorasil column (19 mm by 300 mm), eluting with 19/4.8/76.2/0.1 ethyl acetate/chloroform/hexane/triethylamine at 20 mL/minute to give (E)-1-[4-(7-diethylaminoheptoxy)phenyl]-1,2-diphenyl-2-chloro-ethylene and (Z)-1-[4-(7-diethylaminoheptoxy)phenyl]-1,2-diphenyl-2-chloro-ethylene.

EXAMPLE 28

(E)-1-[4,(7-Diethylaminoheptoxy)phenyl]-1,2-diphenyl-2-chloro-ethylene citrate salt

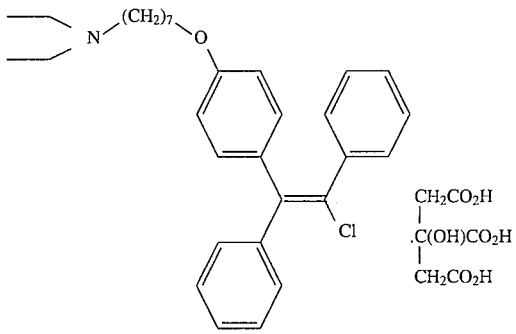

Combine (E)-1-[4-(7-diethylaminoheptoxy)phenyl]-1,2-diphenyl-2-chloro-ethylene (0.225 g) and hot isopropyl alcohol (4 mL). Add a solution of citric acid (0.090 g) in hot isopropyl alcohol (2 mL). Allow to cool and evaporate until a solid forms. Filter and dry to give the title compound: mp; 106°–108° C.

EXAMPLE 29

(Z)-1-[4-(7-Diethylaminoheptoxy)phenyl]-1,2-diphenyl-2-chloro-ethylene citrate salt

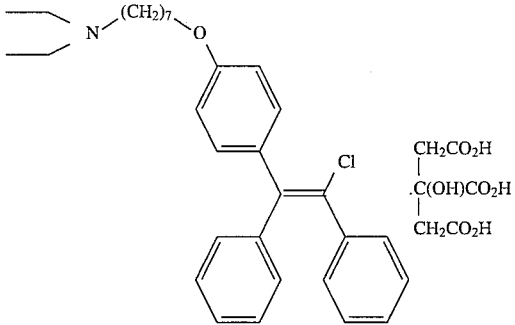

Combine (Z)-1-[4-(7-diethylaminoheptoxy)phenyl]-1,2-diphenyl-2-chloro-ethylene (0.087 g) and hot isopropyl alcohol (3 mL). Add a solution of citric acid (0.035 g) in hot isopropyl alcohol (1 mL). Allow to cool and evaporate until a solid forms. Filter and dry to give the title compound: mp; 94°–96° C.

EXAMPLE 30

(E and Z)-1-[4-(8-Diethylaminooctoxy)phenyl]-1,2-diphenyl-2-chloro-ethylene

Prepare by the methods taught in Example 23, using 8diethylaminooctanol, and Example 24 to give the title compound. Separate the isomers by HPLC, using multiple injections, using a 5 Hm Spherisorb CN (21.2 mm by 250 mm), eluting with 50/50/chloroform/hexane containing 0.1% triethylamine at 20 mL/minute to give (E)-1-[4-(7diethylaminoheptoxy)phenyl]-1,2-diphenyl- 2-chloro-ethylene and (Z)-1-[4-(7-diethylaminoheptoxy)phenyl]-1,2-diphenyl-2-chloro-ethylene.

EXAMPLE 31

(E)-1-[4-(8-Diethylaminooctoxy)phenyl]-1,2-diphenyl-2-chloro-ethylene citrate salt

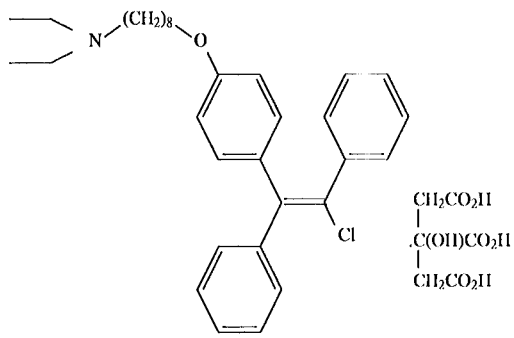

The citrate salt is formed in butanone (2 mL) using (E)-1-(8-diethylaminooctoxy)phenyl]- 1,2-diphenyl-2-chloro-ethylene (0.063 g) and citric acid (0.025 g) to give the title compound: mp; 90°–92° C.

EXAMPLE 32

(Z)-1-[4-(8-Diethylaminooctoxy)phenyl]-1,2-diphenyl-2-chloro-ethylene citrate salt

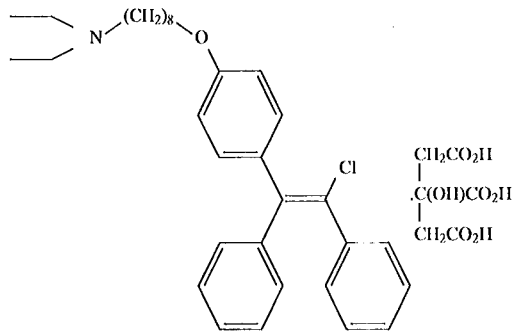

The citrate salt is formed in butanone (0.5 mL) using (Z)-1-[4-(8-diethylaminooctoxy)phenyl]- 1,2-diphenyl-2-chloro-ethylene (0.049 g) and citric acid (0.0094 g): mp; 105° C.

EXAMPLE 33

(E and Z)-1-[4-(9-Diethylaminononoxy)phenyl]-1,2-diphenyl-2-chloro-ethylene

Prepare by the methods taught in Example 23, using 9-diethylaminononanol, and Example 24 to give the title compound. Separate the isomers by HPLC, using multiple injections, using a 5 μm Spherisorb CN (21.2 mm by 250 mm), eluting with 40/60/chloroform/hexane containing 0.1% triethylamine at 20 mL/minute to give (E)-1-[4-(9diethylaminononoxy)phenyl]-1,2-diphenyl- 2-chloro-ethylene and (Z)-1-[4-(9-diethylaminononoxy)phenyl]-1,2-diphenyl-2-chloro-ethylene.

EXAMPLE 34

(E)-1-[4-(9-Diethylaminononoxy)phenyl]-1,2-diphenyl-2-chloro-ethylene citrate salt

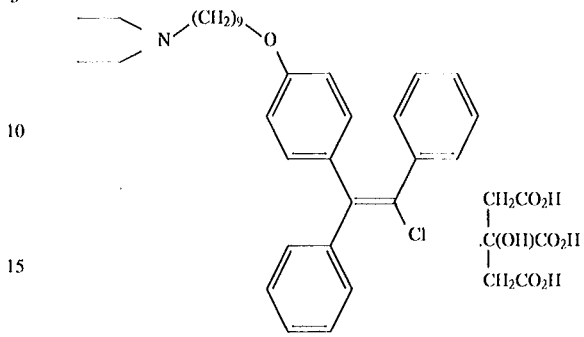

The citrate salt is formed in butanone (2 mL) using (E)-1-[4-( 9-diethylaminononoxy)phenyl]-1,2-diphenyl-2-chloroethylene (0.105 g) and citric acid (0.040 g) in butanone (2 mL) to give the title compound: mp; 92°–3° C.

EXAMPLE 35

(Z)-1-[4-(9-Diethylaminononoxy)phenyl]-1,2,diphenyl-2-chloro-ethylene citrate salt

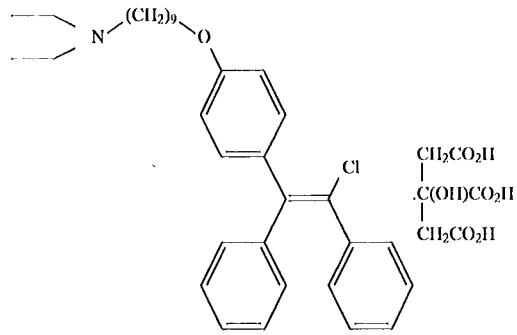

The citrate salt is formed in butanone (0.5 mL) using (Z)-1-[4-( 9-diethylaminononoxy)phenyl]-1,2-diphenyl-2-chloroethylene (0.036 g) and citric acid (0.013 g) in butanone (2 mL) to give the title compound: mp; 83°–85° C.

EXAMPLE 36

(E and Z)-1-[4-(10-Diethylaminodecoxy)phenyl]-1,2-diphenyl-2-chloro-ethylene

Prepare by the methods taught in Example 23, using 10-diethylaminodecanol, and Example 24 to give the title compound. Separate the isomers by HPLC using multiple injections, using a 5 μm Spherisorb CN (21.2 mm by 250 mm), eluting with 30/70/chloroform/hexane containing 0.1% triethylamine at 20 mL/minute to give (E)-1-[4-(10-diethylaminodecoxy)phenyl]-1,2-diphenyl- 2-chloro-ethylene and (Z)-1-[4-(10-diethylaminodecoxy)phenyl]-1,2-diphenyl-2-chloro-ethylene.

EXAMPLE 37

(E)-1-[4-(10-Diethylaminodecoxy)phenyl]-1,2-diphenyl-2-chloro-ethylene citrate salt

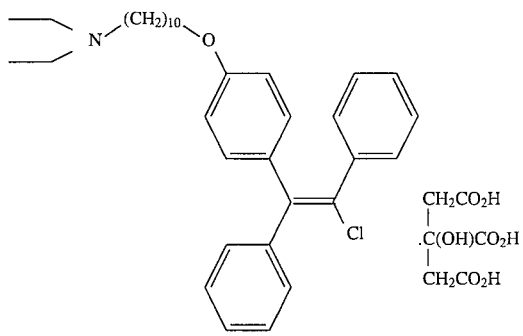

The citrate salt is formed in butanone (2 mL) using (E)-1-[4-( 10-diethylaminodecoxy)phenyl]-1,2-diphenyl-2-chloroethylene (0.092 g) and citric acid (0.034 g) in butanone (0.5 mL) to give the title compound: mp; 94°–95° C.

EXAMPLE 38

(Z)-1-[4-(10-Diethylaminodecoxy)phenyl]-1,2-diphenyl-2-chloro-ethylenecitrate salt

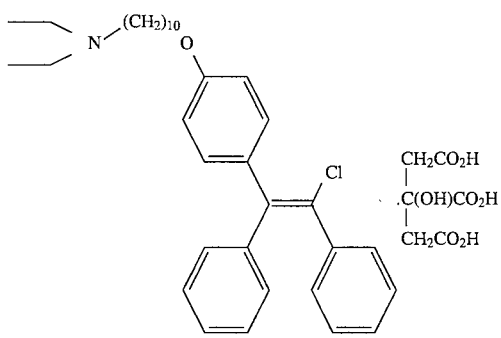

The citrate salt is formed in butanone (0.5 mL) using (Z)-1-4-(10-diethylaminodecoxy)phenyl]- 1,2-diphenyl-2-chloroethylene (0.046 g) and citric acid (0.017 g) in butanone (0.5 mL) to give the title compound: mp; 89°–90° C.

EXAMPLE 39

(E and Z)-1-[4-(11-Diethylaminoundecoxy)phenyl]-1,2-diphenyl-2-chloro-ethylene

Prepare by the methods taught in Example 23, using 11-diethylaminoundecanol, and Example 24 to give the title compound. Separate the isomers by HPLC using multiple injections, using a Lichrosorb RP-18 column (21 mm by 250 mm), eluting with methanol containing 0.05% triethylamine at 20 mL/minute to give (E)-1-[4-(11-diethylaminoundecoxy)phenyl]-1,2-diphenyl- 2-chloro-ethylene and (Z)-1-[4-(11-diethylaminoundecoxy)phenyl]-1,2-diphenyl-2-chloro-ethylene.

EXAMPLE 40

(E)-1-[4-(11-Diethylaminoundecoxy)phenyl]-1,2-diphenyl-2-chloro-ethylene citrate salt

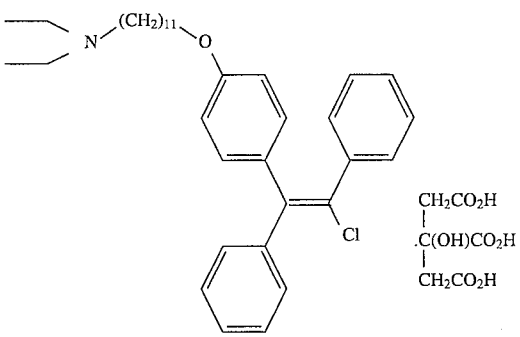

The citrate salt is formed in butanone (2 mL) using (E)-1-[4-( 11-diethylaminoundecoxy)phenyl]-1,2-diphenyl-2-chloroethylene (0.082 g ) and citric acid (0. 029 g ) in butanone (1 mL) to give the title compound: mp; 104°–105° C.

EXAMPLE 41

(Z)-1-[4-(11-Diethylaminoundecoxy)phenyl]-1,2-diphenyl-2-chloro-ethylene citrate salt

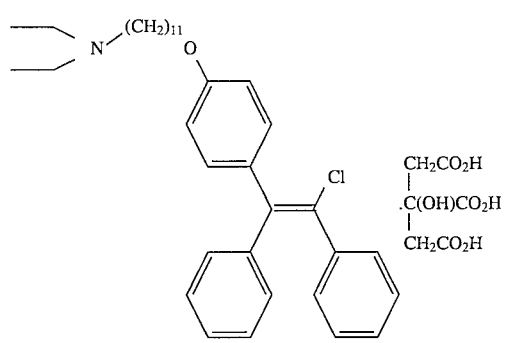

The citrate salt is formed in butanone (2 mL) using (Z)-1-[4-( 11-diethylaminoundecoxy)phenyl]-1,2-diphenyl-2-chloroethylene (0.0284 g) and citric acid (0.0102 g) in butanone (1 mL) to give the title compound: mp; 89°–92° C.

EXAMPLE 42

(E and Z)-1-[4-(12-Diethylaminododecoxy)phenyl]-1,2-diphenyl-2-chloro-ethylene

Prepare by the methods taught in Example 23, using 12-diethylaminododecanol, and Example 24. Separate the isomers by HPLC using multiple injections, using a Lichrosorb RP-18 column column (21 mm by 250 mm), eluting with methanol containing 0.05% triethylamine at 20 mL/minute to give (E)-1-[4-( 12-diethylaminododecoxy)phenyl]-1,2-diphenyl-2-chloroethylene and (Z)-1-[4-(12-diethylaminododecoxy)phenyl]-1,2-diphenyl-2-chloro-ethylene.

EXAMPLE 43

(E)-1-[4,(12-Diethylaminododecoxy)phenyl]-1,2-diphenyl-2-chloro-ethylene citrate salt

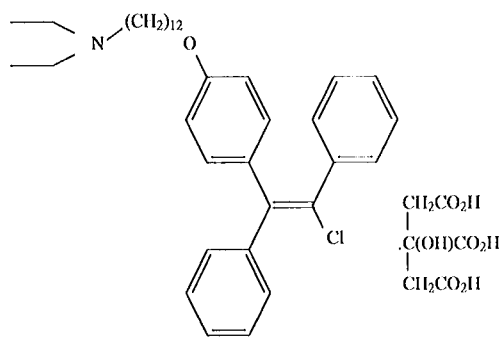

The citrate salt is formed in butanone (2 mL) using (E)-1-[4-(12-diethylaminododecoxy)phenyl]-1,2-diphenyl-2-chloroethylene: mp; 96°–98° C., (0.090 g) and citric acid (0.031 g) in butanone (0.5 mL) to give the title compound: mp; 96°–98° C.

EXAMPLE 44

(Z)-1-[4-(12-Diethylaminododecoxy)phenyl]-1,2-diphenyl-2-chloro-ethylene citrate salt

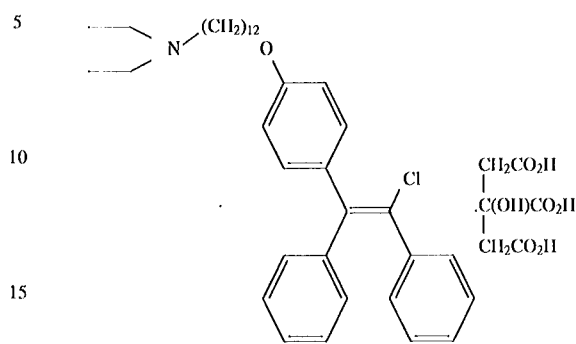

The citrate salt is formed in butanone (2 mL) using (Z)-1-[4-(12-diethylaminododecoxy)phenyl]-1,2-diphenyl-2-chloroethylene (0.032 g) and citric acid (0.011 g) to give the title compound: mp; 98°–100° C.

The compounds of Formula I and Formula II in which Y is NH can be prepared as described in Scheme C. All substituents, unless otherwise indicated, are previously defined. The reagents and starting materials are readily available to one of ordinary skill in the art.

SCHEME C

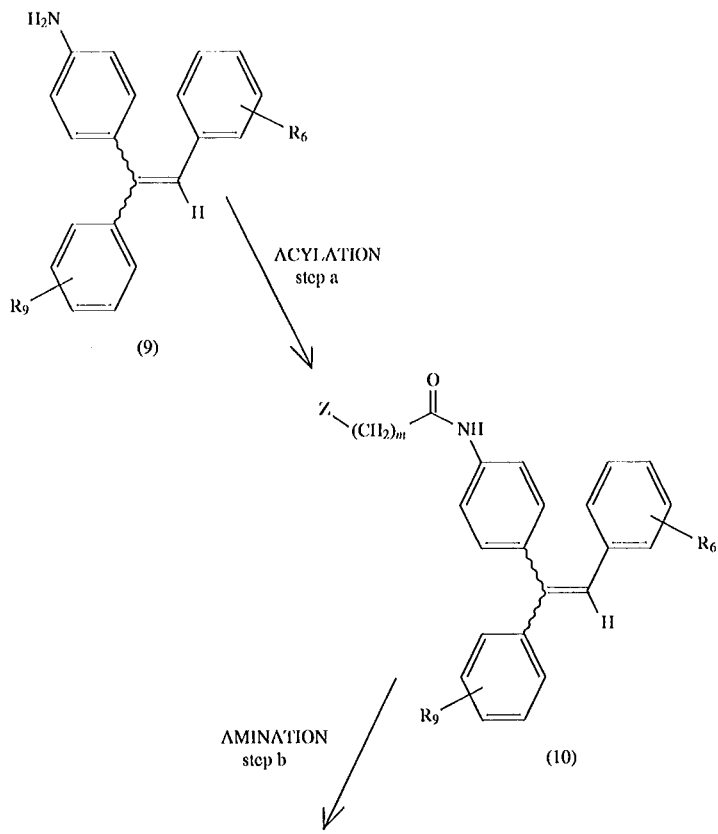

-continued
SCHEME C
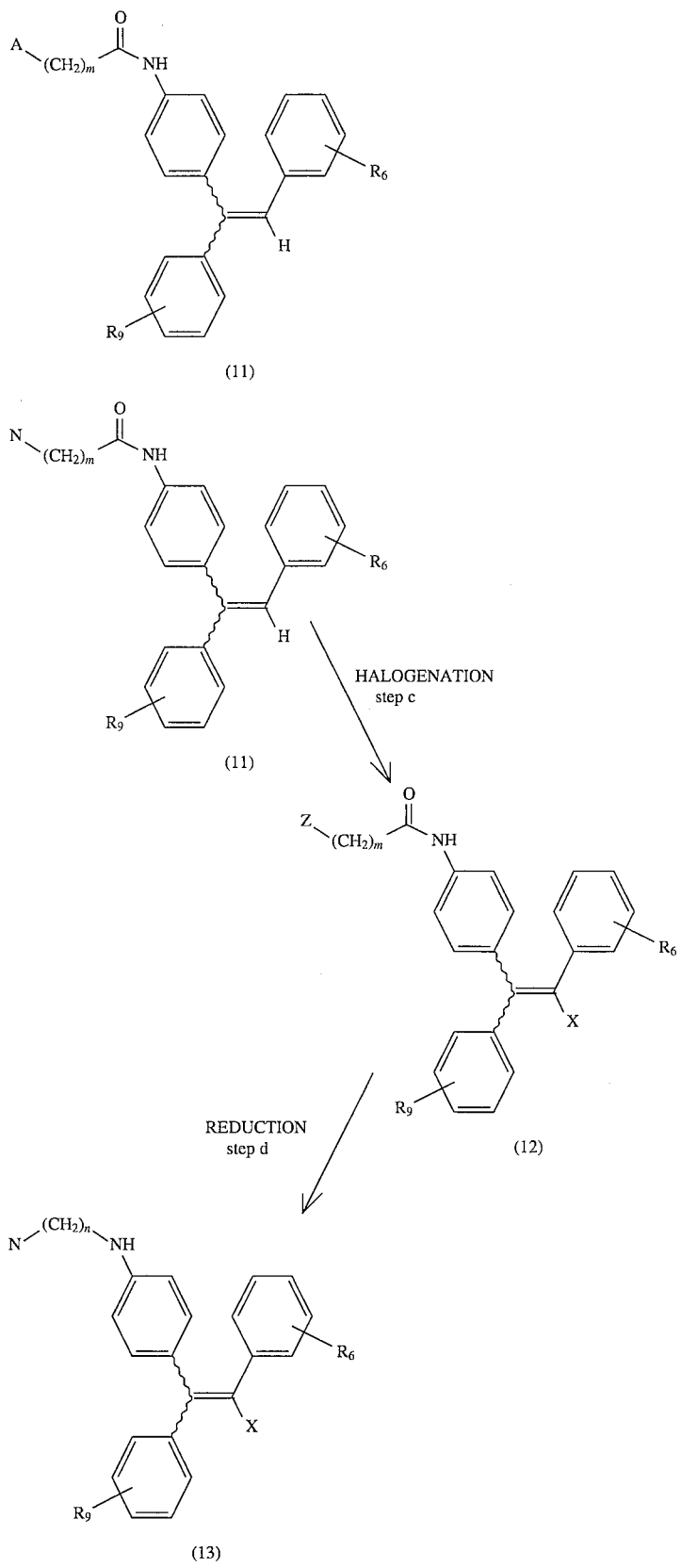

-continued
SCHEME C

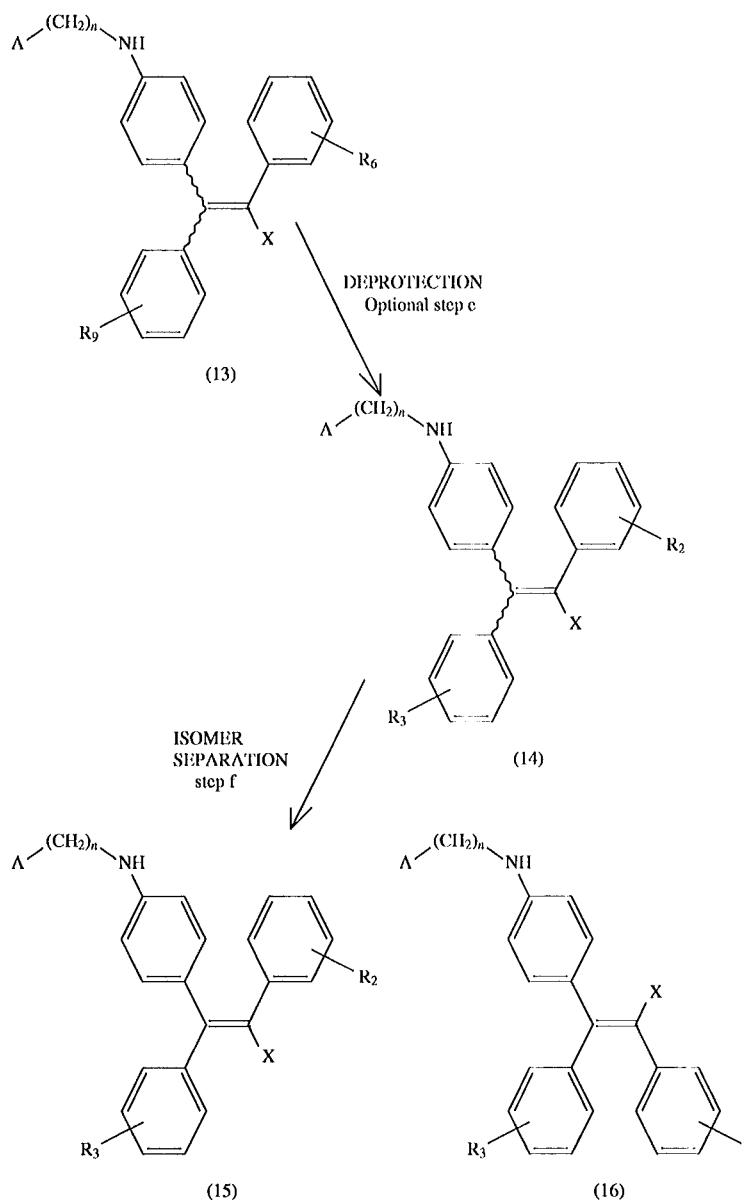

In Scheme C, step a, an appropriate ω-haloalkylacid halide, Z—(CH$_2$)$_m$—C(O)Z$_1$, is added to an appropriate amino-triaryl-ethylene of structure 9 in an acylation reaction to give a ω-haloalkylamido-triaryl-ethylene of structure 10.

An appropriate ω-haloalkylacid halide, Z—(CH$_2$)$_m$—C(O)Z$_1$, is one in which m is 1 less than n as defined above and as desired in the final product of Formula I and Formula II and Z and Z$_1$ may each independently be a chlorine atom or a bromine atom. An appropriate amino-triaryl-ethylene of the structure 9 is one in which R$_6$ is R$_2$ as defined above, or is a suitably protected hydroxy which after deprotection provide compounds of Formula I and Formula II in which R$_2$ is a hydroxy group; R$_9$ is R$_3$ as defined above, or is a suitably protected hydroxy which after deprotection provide compounds of Formula I and Formula II in which R$_3$ is a hydroxy group, or R$_9$ is an amino group, a protected amino group, or a group which gives rise to an amino group, such as a nitro group. Appropriate amino-triaryl-ethylenes of the structure 9 are readily prepared by methods analogous to those used to prepare triaryl-ethylene of structure 1 described in U.S. Pat. No. 2,914,563, R. E. Allen et al; U.S. Pat. No. 2,429,556, C. F. Longfellow et al; and syn. Comm. 17, 1787–1796 (1987), M. I. Al-Hassan.

For example, a slight molar excess of a ω-haloalkylacid halide is contacted with a amino-triaryl-ethylene of the structure 9 in a suitable solvent, such as pyridine, dimethylformamide, acetonitrile, or tetrahydrofuran. The reaction is carried out in the presence of a suitable base, such as pyridine, triethylamine, sodium carbonate, or sodium bicarbonate. The reaction may be carried out in the presence of a catalyst, such as 4-dimethylaminopyridine. The reaction is stirred for from 1–72 hours. The production of a compound of Formula I and II in which R$_3$ is —NH(CH$_2$)$_p$A$_1$ wherein p=n and A=A$_1$ requires the use of a compound of structure 1 in which R$_9$ is amino and slightly more than two molar equivalents of a ω-haloalkylacid halide and gives rise to a compound of structure 10 which is a bis-ω-haloalkylamido-triaryl-ethylene. The product can be isolated and purified by techniques well known in the art. For example, the reaction mixture can be concentrated in vacuo to give a residue. The residue can be chromatographed on silica gel using a suitable organic eluent. The material obtained from chromatography can be recrystallized to give a ω-haloalkylamido-triaryl-ethylene of structure 10.

In Scheme C, step b, a ω-haloalkylamido-triaryl-ethylene of structure 10 is contacted in an amination reaction with an appropriate amine, $HNRR_1$, in which R and $R_1$ are as defined above, morpholine, piperidine, piperazine, 4-methylpiparizine, or pyrrolidine to give ω-aminoalkylamido-triaryl-ethylene of structure 11.

For example, a ω-haloalkylamido-triaryl-ethylene of structure 10 is contacted with a large molar excess of an appropriate amine. A large molar excess of amine is used so that the amine also acts as a base to take up the acid liberated in the reaction. The reaction is carried out in a suitable solvent, such as ethanol, methanol, water, ethanol/water mixtures, or methanol/water mixtures. The reaction may be carried out in the presence of a suitable catalyst, such as potassium iodide. The reaction vessel may be sealed to prevent the escape of volatile amines. The reaction mixture is heated to temperatures of from 40° C. to 100° C. For compounds of structure 10 in which $R_9$ is a ω-haloalkylamido group the use of an additional portion of an appropriate amine gives a bis-ω-aminoalkylamido-triaryl-ethylene which gives rise to a compound of Formula I and II in which $R_3$ is —$NH(CH_2)_pA_1$ wherein p=n and A=$A_1$. The product is isolated from the reaction zone by evaporation or extraction and is purified by chromatography or salt formation and recrystallization to give a ω-aminoalkylamido-triaryl-ethylene of structure 11.

In Scheme C, step c, a ω-aminoalkylamido-triaryl-ethylene of structure 11 are chlorinated or brominated to give ω-aminoalkylamido-triaryl-ethylene of structure 12.

For example, a ω-aminoalkylamido-triaryl-ethylene of structure 11 is contacted with a molar excess of chlorine, bromine, N-chlorosuccinimide, or N-bromosuccinimide in a solvent, such as chloroform or dichloromethane. The reaction is carried out at temperatures from ambient temperature to the reflux temperature of the solvent. After stirring for from 12–72 hours the product can be isolated and purified by techniques well known in the art. For example, the reaction mixture can be concentrated in vacuo and the product purified by chromatography or by recrystallization to give a ω-aminoalkylamido-triaryl-ethylene of structure 12.

In Scheme C, step d, a ω-aminoalkylamido-triaryl-ethylene of structure 12 is contacted with an appropriate reducing agent in a reduction reaction to give a ω-aminoalkylamino-triaryl-ethylene of structure 13.

An appropriate reducing agent is one that will reduce the amido group of a ω-aminoalkylamido-triaryl-ethylene of structure 12 without effecting the other groups present in the compound. The selection and use of such reducing agents is well known and appreciated in the art.

For example, a ω-aminoalkylamido-triaryl-ethylene of structure 12 is contacted with a molar excess of an appropriate reducing agent, such as lithium aluminum hydride, borane, or borane complexes. The reaction is carried out in a solvent, such as diethyl ether or tetrahydrofuran when the appropriate reducing agent is lithium aluminum hydride, or dichloromethane or chloroform when the appropriate reducing agent is borane. The reaction is carried out at temperatures from ambient to the refluxing temperature of the solvent. For compounds of structure 12 in which $R_9$ is a ω-aminoalkylamido group the use of an additional portion of the appropriate reducing agent gives a bis-ω-aminoalkylamino-triaryl-ethylene which gives rise to a compound of Formula I and II in which $R_3$ is —$NH(CH_2)_pA_1$ wherein p=n and A=$A_1$. The product can be isolated from the reaction zone by techniques well known in the art, such as quenching, extraction, and evaporation; and may be purified by methods well known in the art, such as chromatography and recrystallization to give a ω-aminoalkylamino-triaryl-ethylene of structure 13.

In Scheme C, Optional step e, for ω-aminoalkylamino-triaryl-ethylene of structure 13 in which $R_6$ or $R_9$ are a protected hydroxy group the protecting group is removed in a deprotection step to provide ω-aminoalkylamino-triaryl-ethylene of structure 14 in which either, $R_2$ or $R_3$, or $R_2$ and $R_3$, are hydroxy as desired in the final product of Formula I and Formula II. Additionally, for ω-aminoalkylamino-triaryl-ethylene of structure 13 in which $R_9$ is a protected amino group is deprotected to provide ω-aminoalkylamino-triaryl-ethylene of structure 14 in which $R_9$ is an amino group can be, by sequentially performing the steps of Scheme C, used as an intermediate for the preparation of a compound of Formula I and Formula II in which $R_3$ is —$NH(CH_2)_pA_1$ wherein p≠n and either A=$A_1$ or A≠$A_1$ or in which $R_3$ is —$NH(CH_2)_pA_1$ wherein p≠n and A≠$A_1$. The removal of amine protecting groups utilizing suitable protecting groups such as those described in *Protecting Groups in Organic synthesis* by T. Greene is well known and appreciated by those skilled in the art.

The selection, use, removal, and sequential removal of suitable hydroxy protecting groups, such as benzyl, p-methoxybenzyl, methyl, t-butyldimethylsilyl, and acetyl, is well known and appreciated in the art and described in *Protecting Groups in Organic Synthesis* by T. Greene.

In Scheme C, step f, the isomers of a ω-aminoalkylamino-triaryl-ethylene of structure 13 or 14 are separated to give a (E)-ω-aminoalkylamino-triaryl-ethylene and the (Z)-ω-aminoalkylamino-triaryl-ethylene.

For example, the isomers of compounds of structure 13 or 14 can be separated and purified by high-performance liquid chromatography or fractional recrystallization of salt to give a (E)-ω-aminoalkylamino-triaryl-ethylene and the (Z)-ω-aminoalkylamino-triaryl-ethylene.

Pharmaceutically acceptable salts of a (E)-ω-aminoalkylamino-triaryl-ethylene and of a (Z)-ω-aminoalkylamino-triaryl-ethylene can be formed in an additional step as is well known and practiced in the art.

The following examples present typical syntheses as described in Scheme C. These examples are understood to be illustrative only and are not intended to limit the scope of the invention in any way. As used in the following examples, the following terms have the meanings indicated: "g" refers to grams, "mg" refers to milligrams, "mmol" refers to millimoles, "mL" refers to milliliters, "mm" refers to millimeters, "°C." refers to degrees Celsius, "$R_f$" refers to retention factor, "mp" refers to melting point, "HPLC" refers to high performance liquid chromatography.

EXAMPLE 45

(E and Z)-1-[4-N-(4-Chlorobutyrylamino)phenyl]-1,2-diphenylethylene

Combine (E and Z)-1-[(4-amino)phenyl]-1,2-diphenylethylene (0.57 g, 2.1 mmol), 4-chlorobutyryl chloride (0.338 g, 2.4 mmol), and dimethylaminopyridine (10 mg) in pyridine (5 mL). Stir under an inert atmosphere for 16 hours. Evaporate in vacuo to give a residue. Dilute with dichloromethane and extract 3 times with 3M hydrochloric acid solution. Dry the organic layer over MgSO$_4$, filter, and evaporate in vacuo to give the title compound.

EXAMPLE 46

(E and Z)-1-[4-N-(4-Diethylaminobutylamino)phenyl]-1,2-diphenyl-ethylene

Combine (E and Z)-1-[4-N-(4-chlorobutyrylamino)phenyl]-1,2-diphenyl-ethylene (3.2 g, 11.8 mmol), diethylamine (30.0 mL), potassium iodide (100 mg, 0.66 mmol), and water (2.0 mL) and seal in a pressure vessel. Heat to 100° C. for 4 hours. Cool to ambient temperature and carefully open the vessel. Evaporate in vacuo. Dilute with dichloromethane and extract with water. Dry the organic layer over MgSO$_4$, filter, and evaporate in vacuo. Chromatograph on silica gel eluting with 10% methanol/dichloromethane. Combine product containing fractions and concentrate in vacuo to give the title compound.

EXAMPLE 47

(E and Z)-1-[4-N-(4-Diethylaminobutyrylamino)phenyl]-1,2-diphenyl-2-chloro-ethylene Combine (E and Z)-1-[4-N-(4-diethylaminobutyrylamino)phenyl]-1,2-diphenyl-ethylene (1.0 g, 2.4 mmol) and N-chlorosuccinimide (0.80 g, 6.0 mmol) in dichloromethane (15 mL). Heat to reflux and stir at reflux for 48 hours. Cool to ambient temperature. Chromatograph on silica gel eluting with 10% methanol/dichloromethane. Combine product containing fractions and concentrate in vacuo to give the title compound.

EXAMPLE 48

(E and Z)-1-[4-(4-Diethylaminobutylamino)phenyl]-1,2,-diphenyl-2-chloro-ethylene

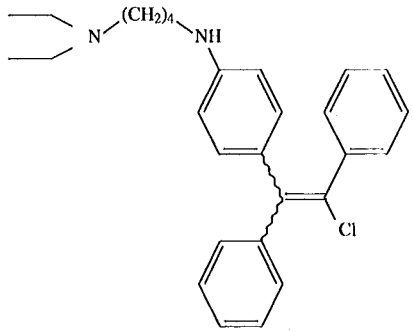

Combine (E and Z)-1-[4-N-(4-diethylaminobutyrylamino)phenyl]-1,2-diphenyl-2-chloroethylene (0.55 g, 1.23 mmol) and borane (5 mL, 1 M in tetrahydrofuran, 5.0 mmol) in THF (10 mL). Heat to reflux and stir at reflux for 20 hours. Quench with methanol and evaporate in vacuo. Partition between dichloromethane and water. Separate the organic layer and dry over MgSO$_4$, filter and evaporate in vacuo. Chromatograph on silica gel to give the title compound.

In a further embodiment, the present invention provides a method for the treatment of a patient afflicted with a neoplastic disease state comprising the administration thereto of a therapeutically effective antineoplastic amount of a compound of Formula I or II.

The term "neoplastic disease state" as used herein refers to an abnormal state or condition characterized by rapidly proliferating cell growth or neoplasm. Neoplastic disease states for which treatment with a compound of Formula I or II will be particularly useful include: Leukemias such as, but not limited to, acute lymphoblastic, chronic lymphocytic, acute myeloblastic and chronic myelocytic; Carcinomas and Adenocarcinomas, such as, but not limited to, those of the cervix, breast, prostate, esophagus, stomach, small intestines, colon and lungs; Sarcomas, such as, but not limited to, oesteroma, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, folicullar reticulum, cell sarcoma and Hodgkins Disease. Neoplastic disease states for which treatment with a compound of Formula I and II will be particularly preferred are neoplastic disease states that are hormone-dependent including: solid tumors of the breast, uterus, and cervix.

As used herein, a "therapeutically effective antineoplastic amount" of a compound of Formula I or II refers to an amount which is effective, upon single or multiple dose administration to the patient, in controlling the growth of the neoplasm or in prolonging the survivability of the patient beyond that expected in the absence of such treatment. As used herein, "controlling the growth" of the neoplasm refers to slowing, interrupting, arresting or stopping its growth and metastases and does not necessarily indicate a total elimination of the neoplasm.

In a further embodiment, the present invention provides a method for the prophylactic treatment of a patient at risk of developing a neoplastic disease state comprising the administration thereto of a prophylactically effective antineoplastic amount of a compound of Formula I or II.

As used herein, "a prophylactically effective antineoplastic amount" of a compound of Formula I or II refers to an amount which is effective, upon single or multiple dose administration to the patient, in preventing or delaying the occurrence of the onset of a neoplastic disease state.

The identification of those patients who are in need of prophylactic treatment for neoplastic disease states is well within the ability and knowledge of one skilled in the art. The methods for identification of patients which are at risk of developing neoplastic disease states are known and appreciated in the medical arts, such as family history of the development of neoplastic disease states and the presence of risk factors associated with the development of neoplastic disease states. A clinician skilled in the art can readily identify, by the use of clinical tests, physical examination and medical/family history, those patients who are at risk of developing neoplastic disease states and thus readily determine if an individual is a patient in need of prophylactic treatment for neoplastic disease states.

A therapeutically effective antineoplastic amount and a prophylactically effective antineoplastic amount can be readily determined by the attending diagnostician, as one skilled in the art, by the use of known techniques and by observing results obtained under analogous circumstances. In determining the therapeutically effective antineoplastic amount or dose, and the prophylactically effective antineoplastic amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances. A therapeutically effective antineoplastic amount and a prophylactically effective antineoplastic amount of a compound of Formula I or II is expected to vary from about 0.1 milligram per kilogram of body weight per day (mg/kg/day) to about 100 mg/kg/day. Preferred amounts are expected to vary from about 0.5 to about 10 mg/kg/day.

In a further embodiment, the present invention provides for the treatment of a patient afflicted with hypercholesterolemia comprising the administration thereto of a therapeutically effective hypocholesterolemic amount of a compound of the Formula I or II.

Hypercholesterolemia is a disease state characterized by levels of serum cholesterol or of LDL cholesterol which are elevated by a clinically significant amount over that considered normal by those of ordinary skill in the art. The identification of those patients who are in need of treatment for hypercholesterolemia is well within the ability and knowledge of one skilled in the art. For example, individuals who have serum cholesterol levels or LDL cholesterol levels, as determined by clinical laboratory tests, which are substantially and chronically elevated over that considered normal by those of ordinary skill in the art, are patients in need of treatment for hypercholesterolemia. By way of further example, individuals who are at risk of developing hypercholesterolemia can also be patients in need of treatment for hypercholesterolemia. A clinician skilled in the art can readily identify, by the use of clinical tests, physical examination and medical/family history, those patients who are suffering from hypercholesterolemia and those who are at risk of developing hypercholesterolemia and thus readily determine if an individual is a patient in need of treatment for hypercholesterolemia.

As used herein, the term a "therapeutically effective hypocholesterolemic amount" refers to an amount which is effective in reducing serum cholesterol levels or LDL cholesterol levels in a patient in need thereof. As such, successful treatment of a patient for hypercholesterolemia is understood to include reducing a patient's serum cholesterol or LDL cholesterol levels. Successful treatment for hypercholesterolemia is also understood to include prophylaxis in preventing clinically significant elevations in serum cholesterol or in LDL cholesterol levels in a patient who is at risk of the development of hypercholesterolemia.

An effective hypocholesterolemic amount can be readily determined by the attending diagnostician, as one skilled in the art, by the use of known techniques and by observing results obtained under analogous circumstances.

In a further embodiment, the present invention provides for the treatment of a patient afflicted with atherosclerosis comprising the administration thereto of a therapeutically effective antiatherosclerotic amount of a compound of the Formula I or II.

Atherosclerosis is a disease state characterized by the development and growth of atherosclerotic lesions or plaque. The identification of those patients who are in need of treatment for atherosclerosis is well within the ability and knowledge of one skilled in the art. For example, individuals who are either suffering from clinically significant atherosclerosis or who are at risk of developing clinically significant atherosclerosis are patients in need of treatment for atherosclerosis. A clinician skilled in the art can readily determine, by the use of clinical tests, physical examination and medical/family history, if an individual is a patient in need of treatment for atherosclerosis.

As used herein a "therapeutically effective antiatherosclerotic amount" of a compound of Formula I or II is an amount which is effective in inhibiting development or growth of atherosclerosis in a patient in need thereof. As such, successful treatment of a patient for atherosclerosis is understood to include effectively slowing, interrupting, arresting, or stopping atherosclerotic lesion or plaque development or growth and does not necessarily indicate a total elimination of the atherosclerosis. It is further understood and appreciated by those skilled in the art that successful treatment for atherosclerosis can include prophylaxis in preventing atherosclerotic lesion or plaque formation.

An effective antiatherosclerotic amount can be readily determined by the attending diagnostician, as one skilled in the art, by the use of known techniques and by observing results obtained under analogous circumstances.

As used herein, the term "patient" refers to a warm-blooded animal, such as a mouse, a rat, a hamster, a WHHL rabbit, or a human, which is afflicted with a particular neoplastic disease state, at risk of developing a neoplastic disease state or who is in need of treatment for atherosclerosis or hypercholesterolemia, such as, for example, in the case of a patient suffering from familial hyperlipidemia.

A therapeutically effective antiatherosclerotic amount and a therapeutically effective hypocholesterolemic amount of a compound of Formula I or II is expected to vary from about 0.1 milligram per kilogram of body weight per day (mg/kg/day) to about 100 mg/kg/day. Preferred amounts are expected to vary from about 0.5 to about 10 mg/kg/day.

In effecting treatment of a patient afflicted with the disease states described above or in effecting prophylactic treatment of a patient who may be afflicted with the disease states as described above, a compound of Formula I or II can be administered in any form or mode which makes the compound bioavailable in effective amounts, including oral and parenteral routes. For example, compounds of Formula I or II can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of Formula I or II in admixture or otherwise in association with one or more inert carriers. These compositions are useful, for example, as assay standards, as convenient means of making bulk shipments, or as pharmaceutical compositions. An assayable amount of a compound of Formula I or II is an amount which is readily measurable by standard assay procedures and techniques as are well known and appreciated by those skilled in the art. Assayable amounts of a compound of Formula I or II will generally vary from about 0.001% to about 75% of the composition by weight. Inert carriers can be any material which does not degrade or otherwise covalently react with a compound of Formula I or II. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising a therapeutically effective amount or prophylactically effective amount of a compound of Formula I or II in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterorex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of Formulas I and II in their end-use application.

With respect to the substituent X, compounds of Formula I and II wherein X is chloro are generally preferred.

With respect to the substituent A, compounds of Formula I and II wherein A is

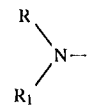

wherein R and $R_1$ are ethyl are generally preferred.

The following example provides an illustration of the utility of the compounds of the present invention. This example is understood to be illustrative only and is not intended to limit the scope of the invention in any way. As used herein, the following terms have the meanings as indicated below: "mL" refers to milliliters; "mg" refers to milligrams; "mmol" refers to millimoles; "$mm^3$" refers to millimeters cubed; "kg" refers to kilograms; "mM" refers to millimolar; "Ga" refers to gauge.

EXAMPLE 49

INHIBITORY EFFECTS OF COMPOUNDS ON TUMOR SIZE

MCF-7 and ZR-75-1 tumors were established in female nude (athymic) mice by the subcutaneous injection of from $1 \times 10^6$ to $2 \times 10^6$ cells from nearly confluent cell cultures. The mice also had a 0.25 mg estradiol pellet implanted subcutaneously because these tumors cells are known to be dependent on estrogens for their growth. Tumors formed from the injected cells were passaged serially by excising the tumors and cutting them into approximately 3 $mm^3$ pieces, after which these pieces were implanted subcutaneously into naive nude mice using a 10 Ga trocar. Usually the tumors were allowed to develop for 2–3 weeks before drug treatments were initiated.

The drug to be administered was dissolved in a small volume of dimethyl sulfoxide and then diluted for injection in a solution of 0.9% saline containing 0.1 mM citric acid, 6.25% ethanol and 3.75% Tween 80. The drug, in 0.2 mL, was then administered by intraperitoneal injection to the mice. Tumors were measured weekly in two dimensions using a Vernier caliper and the tumor volumes were calculated using the formula: $\{(length \times width^2) \div 2\}$ where the width is the shorter of the two measurements.

Inhibition of MCF-7 Human Breast Tumor Growth by Daily Intraperitoneal Administration of (E)-1-[4-(2-diethylaminoethoxy)phenyl]-1,2-diphenyl-2-chloro-ethylene, trans-Clomiphene

| days | control | 0.05 mg/kg | 0.1 mg | 0.2 mg | 0.5 mg |
|---|---|---|---|---|---|
| 21 | 56 ± 7 | 77 ± 14 | 70 ± 14 | 63 ± 15 | 42 ± 3 |
| 32 | 138 ± 18 | 183 ± 41 | 160 ± 35 | 118 ± 33 | 72 ± 12 |
| 39 | 195 ± 24 | 233 ± 65 | 235 ± 53 | 150 ± 41 | 73 ± 13 |
| 46 | 263 ± 42 | 305 ± 76 | 307 ± 63 | 201 ± 41 | 85 ± 15 |
| 53 | 365 ± 67 | 366 ± 136 | 401 ± 114 | 216 ± 41 | 95 ± 23 |
| 60 | 447 ± 69 | 407 ± 154 | 442 ± 124 | 205 ± 83 | 94 ± 27 |

Inhibition of MCF-7 Human Breast Tumor Growth by Daily Intraperitoneal Administration of (E)-1-[4-(4-diethylaminobutoxy)phenyl]-1,2-diphenyl-2-chloro-ethylene

| days | control | 0.02 mg | 0.05 mg | 0.1 mg | 0.2 mg |
|---|---|---|---|---|---|
| 20 | 63 ± 6 | 58 ± 9 | 65 ± 10 | 70 ± 9 | 55 ± 10 |
| 27 | 171 ± 27 | 98 ± 17 | 95 ± 17 | 76 ± 13 | 57 ± 10 |
| 34 | 302 ± 53 | 109 ± 20 | 134 ± 27 | 79 ± 19 | 56 ± 12 |
| 41 | 438 ± 74 | 128 ± 29 | 123 ± 23 | 77 ± 14 | 50 ± 11 |
| 48 | 571 ± 95 | 153 ± 39 | 126 ± 30 | 75 ± 17 | 58 ± 15 |
| 55 | 715 ± 125 | 158 ± 50 | 127 ± 32 | 83 ± 30 | 52 ± 13 |
| 62 | 1040 ± 193 | 155 ± 25 | 170 ± 35 | 116 ± 48 | 55 ± 12 |
| 69 | 1200 ± 246 | 163 ± 24 | 164 ± 39 | 111 ± 54 | 53 ± 13 |

Inhibition of MCF-7 Human Breast Tumor Growth by Daily Intraperitoneal Administration of (E)-1-[4-(4-diethylaminobutoxy)phenyl]-1,2-diphenyl-2-chloro-ethylene

| days | control | 0.005 mg | 0.01 mg/kg | 0.02 mg/kg | 0.05 mg/kg | 0.1 mg/kg |
|---|---|---|---|---|---|---|
| 13 | 46 ± 6 | 40 ± 6 | 41 ± 4 | 42 ± 5 | 52 ± 6 | 43 ± 6 |
| 18 | 73 ± 7 | 77 ± 18 | 72 ± 13 | 64 ± 5 | 90 ± 7 | 72 ± 11 |
| 26 | 110 ± 16 | 147 ± 37 | 116 ± 23 | 89 ± 16 | 131 ± 25 | 86 ± 22 |
| 32 | 146 ± 18 | 206 ± 54 | 143 ± 36 | 118 ± 27 | 154 ± 39 | 101 ± 25 |
| 39 | 267 ± 50 | 267 ± 64 | 171 ± 42 | 131 ± 29 | 182 ± 43 | 123 ± 33 |
| 46 | 311 ± 45 | 370 ± 96 | 222 ± 49 | 144 ± 31 | 198 ± 53 | 126 ± 46 |
| 53 | 437 ± 66 | 443 ± 140 | 259 ± 52 | 166 ± 38 | 196 ± 42 | 154 ± 55 |

What is claimed is:

1. A compound of the formula

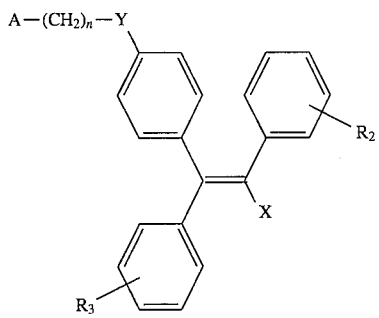

wherein

A is a radical of the formula

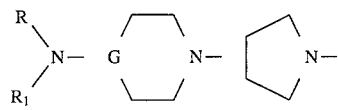

wherein

R and $R_1$ are each independently hydrogen or $C_1$–$C_4$ alkyl; and

G is HN, $H_3$CN, $CH_2$, or O;

n is an integer from 4 to 12;

$R_2$ is hydrogen, $C_1$–$C_4$ alkyl, $C_1$–$C_4$ alkoxy, halogen, or hydroxy;

$R_3$ is hydrogen, $C_1$–$C_4$ alkyl, $C_1$–$C_4$ alkoxy, halogen, hydroxy, or —Y($CH_2$)$_p$$A_1$ in which $A_1$ is a radical of the formula

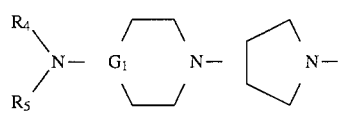

wherein $R_4$ and $R_5$ are each independently hydrogen or $C_1$–$C_4$ alkyl;

G1 is HN, $H_3$CN, $CH_2$, or O; and p is an integer from 4 to 12;

X is chloro or bromo;

Y is O or NH;

or a pharmaceutically acceptable salt thereof.

2. A compound according to claim 1 wherein X is chloro.

3. A compound according to claim 2 wherein Y is O.

4. A compound according to claim 3 wherein A is a radical of the formula

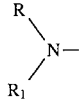

wherein R and $R_1$ are ethyl.

5. The compound (E)-1-[4-(4diethylaminobutoxy)phenyl]-1,2-diphenyl-2-chloroethylene.

6. The compound (E)-1-[4-(5diethylaminopentoxy)phenyl]-1,2-diphenyl-2-chloroethylene.

7. The compound (E)-1-[4-(4diethylaminobutoxy)phenyl]-1-(4-hydroxy)phenyl-2-phenyl- 2-chloro-ethylene.

8. A compound of the formula

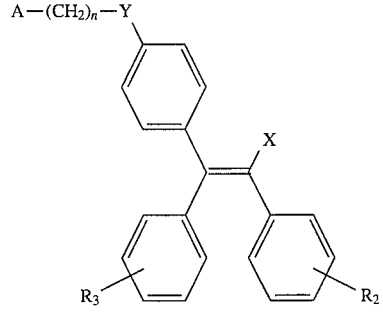

wherein

A is a radical of the formula

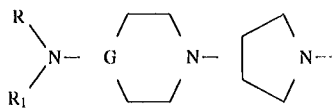

wherein

R and $R_1$ are each independently hydrogen or $C_1$-$C_4$ alkyl; and

G is HN, $H_3$CN, $CH_2$, or O;

n is an integer from 4 to 12;

$R_2$ is hydrogen, $C_1$-$C_4$ alkyl, $C_1$-$C_4$ alkoxy, halogen, or hydroxy;

$R_3$ is hydrogen, $C_1$-$C_4$ alkyl, $C_1$-$C_4$ alkoxy, halogen, hydroxy, or —Y($CH_2$)$_p$$A_1$ in which $A_1$ is a radical of the formula

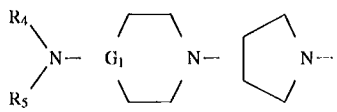

wherein $R_4$ and $R_5$ are each independently hydrogen or $C_1$-$C_4$ alkyl;

G1 is HN, $H_3$CN, $CH_2$, or O; and p is an integer from 4 to 12;

X is chloro or bromo;

Y is O or NH;

or a pharmaceutically acceptable salt thereof.

9. A compound according to claim 8 wherein X is chloro.

10. A compound according to claim 9 wherein Y is O.

11. A compound according to claim 10 wherein A is a radical of the formula

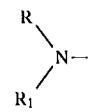

wherein R and $R_1$ are ethyl.

12. The compound (Z)-1-[4-(4diethylaminobutoxy)phenyl]-1,2-diphenyl-2-chloroethylene.

13. The compound (Z)-1-[4-(5diethylaminopentoxy)phenyl]-1,2-diphenyl-2-chloroethylene.

14. The compound (Z)-1-[4-(4diethylaminobutoxy)phenyl]-1-(4-hydroxy)phenyl-2-phenyl- 2-chloro-ethylene.

15. A pharmaceutical composition comprising a therapeutically effective amount of a compound of claims 1 or 8 in admixture or otherwise in association with one or more pharmaceutically acceptable carriers or excipients.

* * * * *

UNITED STATES PATENT AND TRADEMARK OFFICE
CERTIFICATE OF CORRECTION

PATENT NO. : 5,525,633

DATED : June 11, 1996

INVENTOR(S) : Donald P. Matthews, Alan J. Bitonti, William A. Van Sickle, Donald A. Kaplan It is certified that error appears in the above-identified patent and that said Letters Patent is hereby corrected as shown below:

Column 4, Line 59 patent reads: "(4hydrox-" and should read -- (4-hydroxy- --.

Column 5, Line 16 patent reads: "(4hydrox-" and should read -- (4-hydroxy- --.

Column 8, Line 62 patent reads: "RS" and should read -- $R_8$ --.

Column 9, Line 2 patent reads "base gives an bis-" and should read -- base gives a bis- --.

Column 9, Line 18 patent reads "can also acts" and should read -- can also act --.

Column 9, Line 52 patent reads "of a Ω-aminoalkoxy-" and should read -- of a ω-aminoalkoxy- --.

Column 10, Line 14 patent reads "diphenyl,2-chloro-" and should read -- diphenyl-2-chloro- --.

Column 10, Line 55 patent reads "4diethylaminobutoxy)" and should read -- 4-diethylaminobutoxy) --.

Column 11, Line 21 patent reads "mL" and should read -- 3 mL --.

Column 15, Line 56 patent reads "2-phenyl-2-phenyl-2-chloro" and should read -- -2-phenyl-2-chloro --.

Column 15, Line 67 patent reads "hydroxy)-phenyl" and should read -- hydroxy)phenyl --.

Column 16, Line 16 patent reads "and1" and should read -- and 1 -- .

Column 16, Line 46 patent reads "evaporate" and should read -- evaporate in vacuo -- .

Column 16, Line 49 and 50 reads "half Evaporate" and should read -- half. Evaporate --.

Column 16, Line 65 patent reads "4diethylaminobutoxy)" and should read -- (4-diethylaminobutoxy -- .

UNITED STATES PATENT AND TRADEMARK OFFICE
CERTIFICATE OF CORRECTION

PATENT NO. : 5,525,633

DATED : June 11, 1996

INVENTOR(S) : Donald P. Matthews, Alan J. Bitonti, William A. Van Sickle, Donald A. Kaplan It is certified that error appears in the above-identified patent and that said Letters Patent is hereby corrected as shown below:

Column 21, Line 18 patent reads "to-give" and should read -- to give -- .

Column 21, Line 29 patent reads "for from 1214 72" and should read -- for from 12-72 -- .

Column 21, Line 55 patent reads "(CH2)" and should read -- $(CH_2)$ -- .

Column 22, Line 37 patent reads "evaporate Chromatograph" and should read -- evaporate in vacuo. Chromatograph -- .

Column 24, Line 56 patent reads "8diethylaminoocotanol," and should read -- 8-diethylaminooctanol, -- .

Column 24, Line 60 patent reads "7diethylaminoheptoxyl)" and should read --7-diethylaminoheptoxy) -- .

Column 28, Line 61 patent reads "column column" and should read -- column --.

Column 29, Line 1 patent reads "[4," and should read -- [4- --.

Column 34, Line 53 patent reads "syn." and should read -- Syn. --.

Column 34, Line 56 patent reads "a amino" and should read -- an amino --.

Column 43, Line 10 patent reads "0.05 mg/kg" and should read -- 0.05 mg --.

Column 43, Line 37 patent reads "0.01 mg/kg 0.02 mg/kg 0.05 mg/kg 0.1 mg/kg" and should read --0.01 mg 0.02 mg 0.05 mg 0.1 mg --.

UNITED STATES PATENT AND TRADEMARK OFFICE
CERTIFICATE OF CORRECTION

PATENT NO. : 5,525,633

DATED : June 11, 1996

INVENTOR(S) : Donald P. Matthews, Alan J. Bitonti, William A. Van Sickle, Donald A. Kaplan It is certified that error appears in the above-identified patent and that said Letters Patent is hereby corrected as shown below:

Column 44, Line 46 patent read "(4diethylaminobutoxy)" and should read -- (4-diethylaminobutoxy)--.

Column 44, Line 50 patent reads "(4diethylaminobutoxy)' and should read -- (4-diethylaminobutoxy) --.

Column 45, Line 27 patent reads "G1" and should read -- $G_1$ -- as found in Specification on page 75, line 15.

Column 46, Line 16 patent reads "(4diethylaminobutoxy)" and should read -- (4-diethylaminobutoxy) --.

Column 46, Line 20 patent reads "(4diethylaminobutoxy)" and should read -- (4-diethylaminobutoxy) --.

Signed and Sealed this

Twenty-eighth Day of April, 1998

*Attest:*

BRUCE LEHMAN

*Attesting Officer*  *Commissioner of Patents and Trademarks*